(12) United States Patent
Lee et al.

(10) Patent No.: US 10,549,277 B2
(45) Date of Patent: *Feb. 4, 2020

(54) INTEGRATED MICROFLUIDIC PLATFORM FOR SELECTIVE EXTRACTION OF SINGLE-CELL MRNA

(71) Applicant: The Regents of the University of California, Oakland, CA (US)

(72) Inventors: Abraham P. Lee, Irvine, CA (US); H. Kumar Wickramasinghe, Irvine, CA (US); Do-Hyun Lee, Irvine, CA (US); Yinglei Tao, Irvine, CA (US); Xuan Li, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/697,898

(22) Filed: Sep. 7, 2017

(65) Prior Publication Data

US 2018/0078940 A1 Mar. 22, 2018

Related U.S. Application Data

(63) Continuation-in-part of application No. 15/288,969, filed on Oct. 7, 2016, now Pat. No. 9,862,941.

(60) Provisional application No. 62/384,628, filed on Sep. 7, 2016, provisional application No. 62/405,754, filed on Oct. 7, 2016, provisional application No. 62/480,934, filed on Apr. 3, 2017, provisional application No. 62/241,600, filed on Oct. 14, 2015, (Continued)

(51) Int. Cl.
*B01L 3/00* (2006.01)
*C12Q 1/6886* (2018.01)
*C12Q 1/6806* (2018.01)
*C12N 15/10* (2006.01)

(52) U.S. Cl.
CPC ... *B01L 3/502761* (2013.01); *B01L 3/502707* (2013.01); *C12N 15/101* (2013.01); *C12Q 1/6806* (2013.01); *C12Q 1/6886* (2013.01); *B01L 2200/0652* (2013.01); *B01L 2200/0668* (2013.01); *B01L 2200/12* (2013.01); *B01L 2300/044* (2013.01); *B01L 2300/0681* (2013.01); *B01L 2300/0883* (2013.01); *B01L 2300/0887* (2013.01); *B01L 2400/086* (2013.01)

(58) Field of Classification Search
CPC .. B01L 3/50261; C12Q 1/6844; C12N 15/101
See application file for complete search history.

(56) References Cited

U.S. PATENT DOCUMENTS

| | | |
|---|---|---|
| 8,365,311 B2 | 1/2013 | Nawarathna et al. |
| 8,927,040 B2 | 1/2015 | Brand et al. |

(Continued)

OTHER PUBLICATIONS

Sims et al, Fluorogenic DNDNA sequencing in PDMS microreactors, 2011, nature Methods, 8, 575-583. (Year: 2011).*

(Continued)

*Primary Examiner* — Narayan K Bhat
(74) *Attorney, Agent, or Firm* — Knobbe, Martens, Olson & Bear LLP

(57) ABSTRACT

Disclosed is a lab-on-a-chip platform comprising a microfluidic device sealed with a thin membrane. An analysis probe configured to penetrate the thin membrane to access a sample trapped in the microfluidic device.

21 Claims, 16 Drawing Sheets

Specification includes a Sequence Listing.

Related U.S. Application Data provisional application No. 62/384,628, filed on Sep. 7, 2016.

(56) References Cited

U.S. PATENT DOCUMENTS

| | | |
|---|---|---|
| 9,862,941 B2 | 1/2018 | Lee et al. |
| 2002/0182654 A1 | 12/2002 | Jing et al. |
| 2005/0272039 A1 | 12/2005 | Yasuda |
| 2006/0177815 A1 | 8/2006 | Soh et al. |
| 2008/0038807 A1 | 2/2008 | Pommersheim |
| 2011/0059556 A1 | 3/2011 | Strey et al. |
| 2013/0078163 A1 | 3/2013 | Chung et al. |
| 2013/0210649 A1 | 8/2013 | McKnight et al. |

OTHER PUBLICATIONS

International Search Report and Written Opinion of the International Searching Authority for International Application No. PCT/US16/56683, dated Dec. 27, 2016, in 15 pages.

Murata et al, "Electrochemical single-cell gene-expression assay combining dielectrophorectic manipulation with secreted alkaline phosphatase reporter system", 2009, Biosensors and Bioelectronics, 25, pp. 913-919.

Stinson et al., "Genes Expressed in the Male Gametophyte of Flowering Plants and Their Isolation", 1987, Plant Physiol., 82, pp. 442-447.

\* cited by examiner

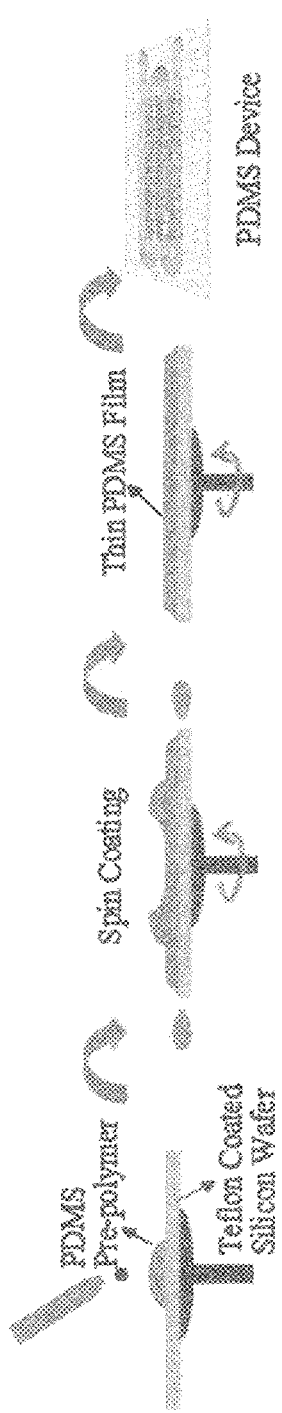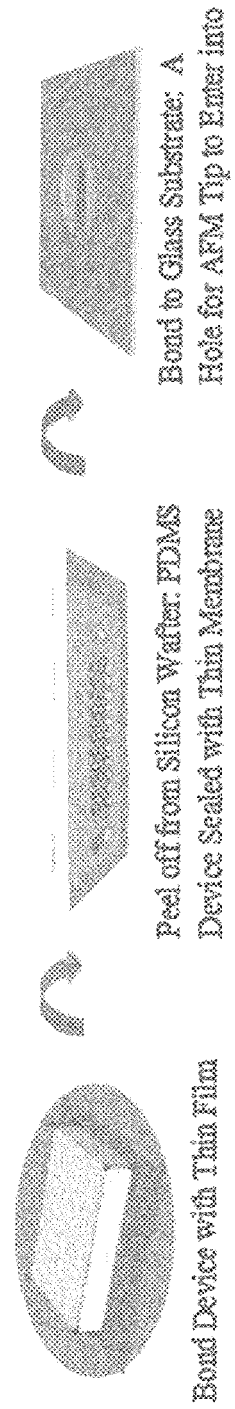

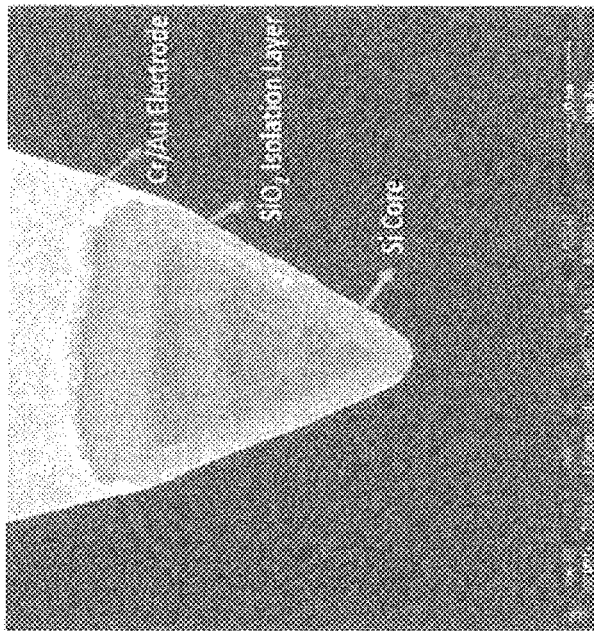
AFM probe after fabrication. Scale Bar: 5µm.
FIG. 4A-1
Zoom-in image of tip-end. Scale Bar: 200nm.
FIG. 4A-2
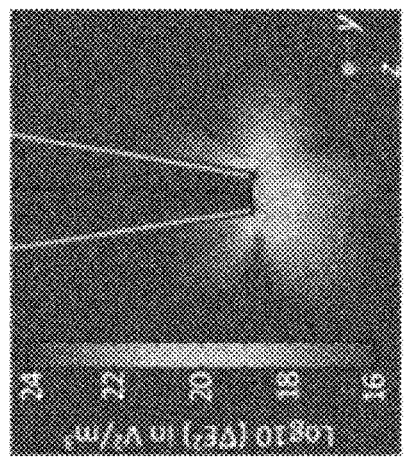
FIG. 4B

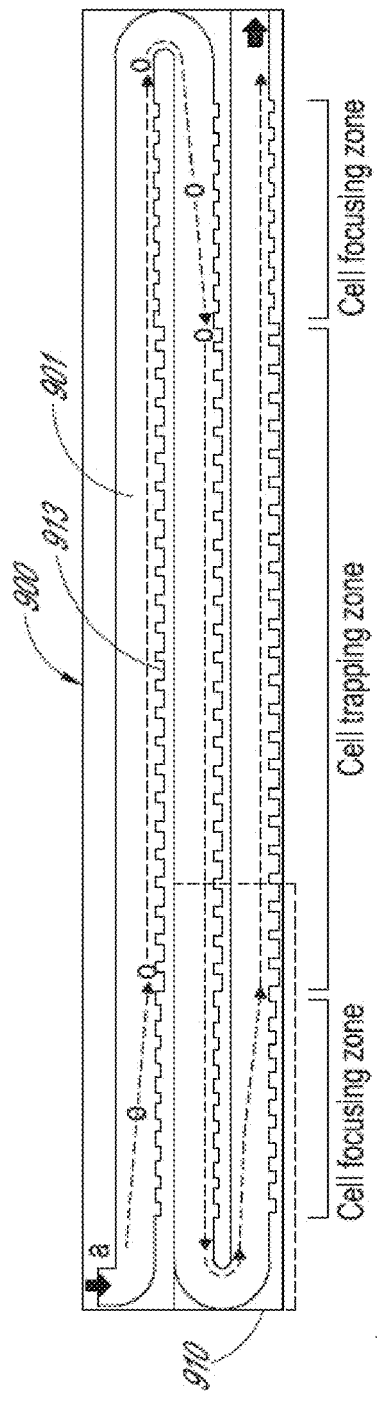
FIG. 5A
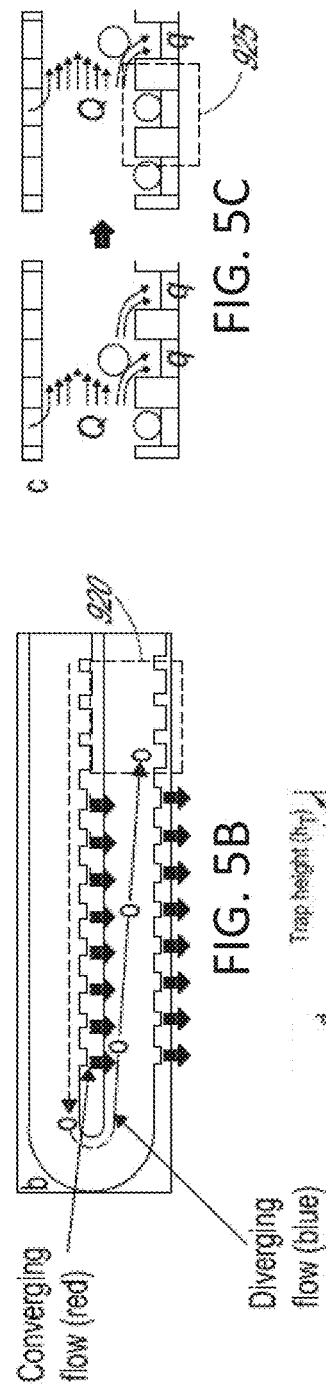
FIG. 5B
FIG. 5C
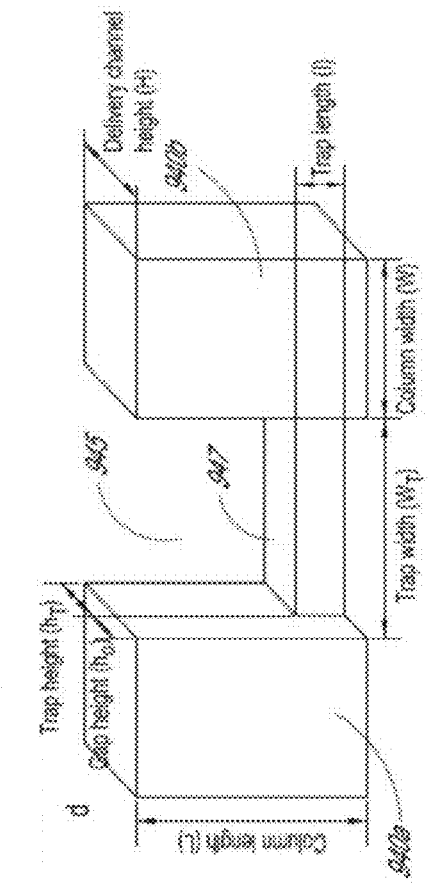
FIG. 5D

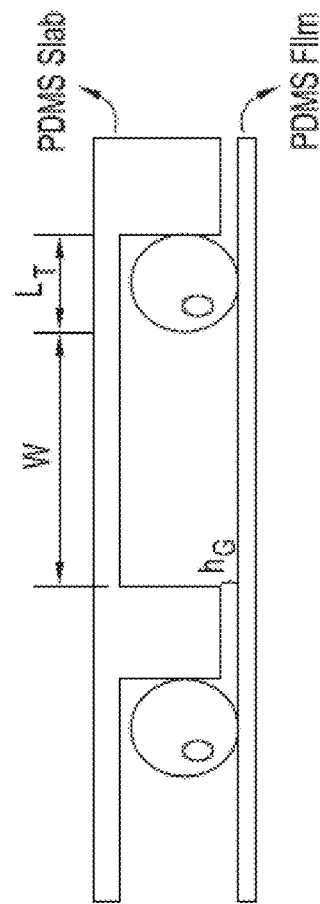
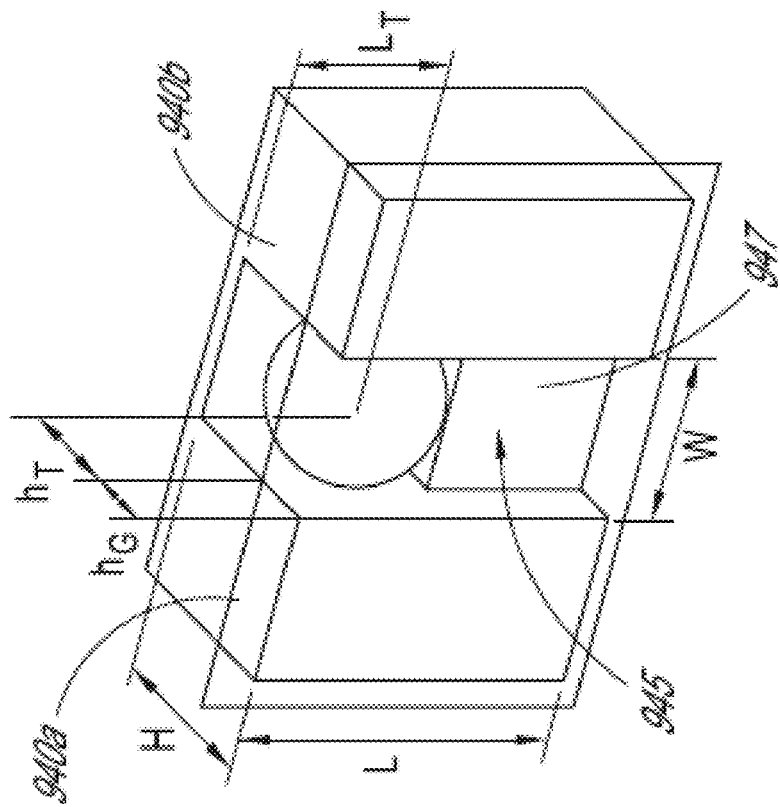
FIG. 7B
FIG. 7A

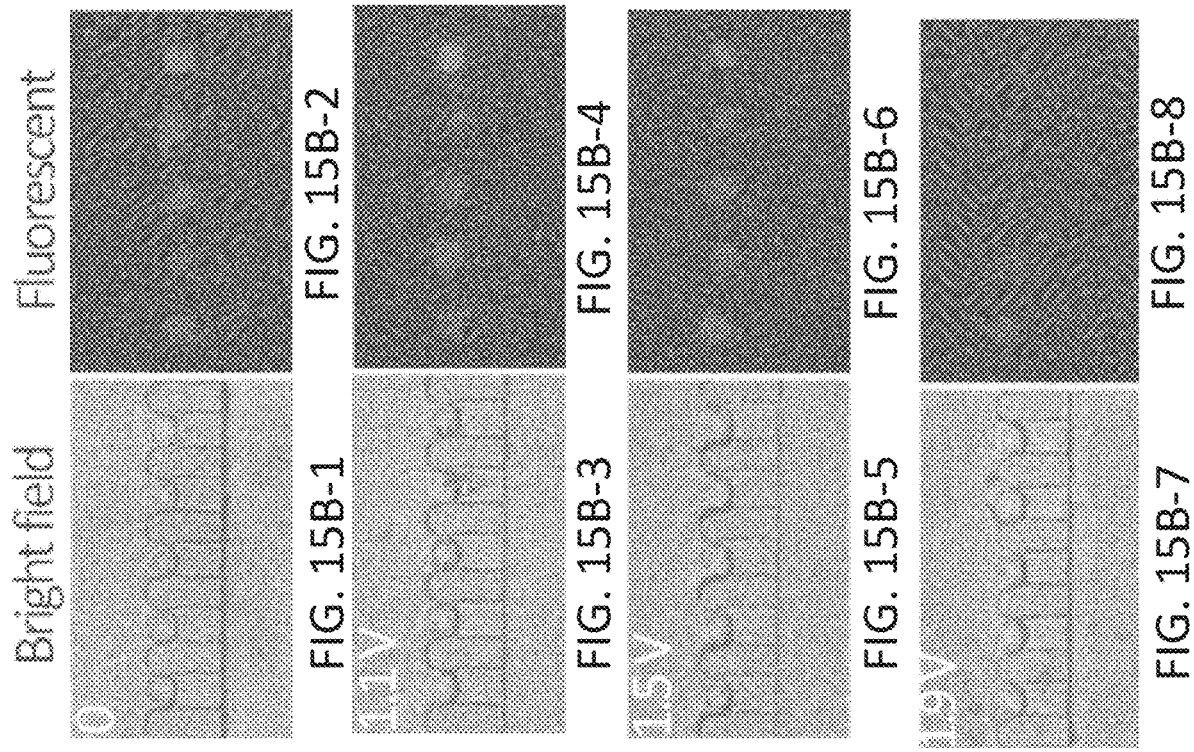
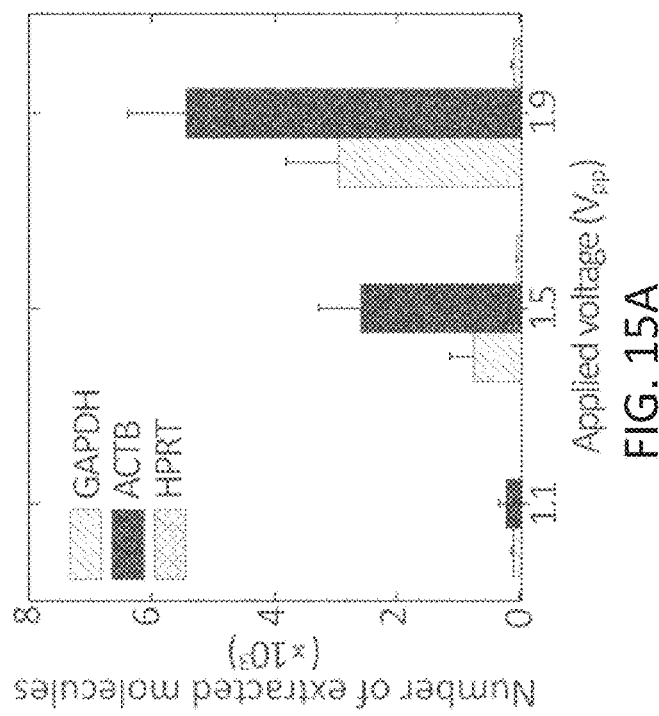

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 1
tcatcaccat tggcaatgag                                            20

<210> SEQ ID NO 2
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 2
actccatgcc caggaagga                                             19

<210> SEQ ID NO 3
<211> LENGTH: 18

```
<212> TYPE: DNA
<213> ORGANISM: Artificial Sequence
<220> FEATURE:
<223> OTHER INFORMATION: oligonucleotide primer

<400> SEQUENCE: 3
tccactggcg tcttcacc                                                  18

<210> SEQ ID NO 4
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 4
ggcagagatg atgacccttt t                                              21

<210> SEQ ID NO 5
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 5
tgaccttgat ttattttgca tacc                                           24

<210> SEQ ID NO 6
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 6
cgagcaagac gttcagtcct                                                20

<210> SEQ ID NO 7
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 7
cggctgactt ccagatatga c                                              21

<210> SEQ ID NO 8
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 8
gctttgccct gtcacaaata c                                              21

<210> SEQ ID NO 9
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 9
```

```
cgcagctcag gaagaatgtg                                              20

<210> SEQ ID NO 10
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 10
tgaagtacac tggcattgac g                                            21

<210> SEQ ID NO 11
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 11
aaaggcccaa gactctctcc                                              20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 12
caagtactcg gggttctcca                                              20
```

INTEGRATED MICROFLUIDIC PLATFORM FOR SELECTIVE EXTRACTION OF SINGLE-CELL MRNA

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 30999802_1.txt, the date of creation of the ASCII text file is Aug. 13, 2019, and the size of the ASCII text file is 2.86 KB.

BACKGROUND

Field

Single-cell analysis provides metabolic and genetic information of individual cells precisely, whereas traditional bulk tests neglect the intracellular heterogeneity and the stochastic effects among cell population, which can be useful in determining key cellular activities. Single-cell analysis, such as, for example, single-cell genotyping by the measurement of mRNAs within a living cell can be advantageous in many biomedical research areas such as cancer diagnostics, rare cell population identification, and so on. The development of high-throughput micro/nanofluidic technologies has made it possible to automate the processing, manipulation, and analysis of populations of single cells. However, most of the current micro/nanofluidic platforms limit all the reactions within the chip and prevent single-cell access by external instruments. In addition, most of the developed single-cell analytical methods require cell lysing and complicated purification procedures to isolate genetic materials, which are not suitable for either monitoring gene expression within a single cell as a function of time in response to various stimuli, or cell retrieval after analysis.

Description of the Related Art

Typically, the probes of atomic force microscopy (AFM) have been used for measuring the roughness of a sample surface at a high resolution, imaging or manipulating of biomolecules, and/or injection of molecules into specific site so accurately. Recent techniques for the extraction and analysis of a range of mRNA species from a single living cell employs a modified AFM probe or a dielectrophoretic nanotweezers (DENT), to attract various kinds of mRNA molecules such as beta-actin, GAPDH (glyceraldehyde 3-phosphate dehydrogenase), and HPRT (hypoxanthine phosphoribosyltransferase) towards its end by dielectrophoresis (DEP) effect. However, the AFM probe in these techniques was moved to a randomly selected cell. Thus, single cells of no interest could be analyzed using these techniques. Additionally, all probing processes in these techniques were performed under an open environment, thus increasing chances that media is accidentally evaporated.

SUMMARY

The embodiments disclosed herein comprise an integrated platform through the combination of a high-density single-cell trapping array and a modified AFM probing system for the extraction of intracellular molecules (e.g. mRNAs, proteins, small molecules) from an individual cell. The platform can facilitate single-cell transcriptomic analysis to reveal in-depth information of cellular mechanisms and population heterogeneity. Microfluidic technology can be advantageously used for automation of single-cell sorting, trapping and identification. However, many of the existing microfluidic devices can be closed off and prevent single-cell access by external analytical equipment. Moreover, mRNA extraction in current microfluidic systems can require cell lysis which destroys the cells.

In contrast the systems and methods described herein are configured to extract mRNA from the cells without destroying the cells. Additionally, the systems and methods described herein can control the mRNA extraction with substantial precision. In various embodiments of the integrated platform described herein, cells can be trapped individually in a microwell array sealed by a 1-μm thick polydimethylsiloxane (PDMS) membrane. The 1-μm-thick ultra-thin PDMS membrane can be bonded (e.g., irreversibly bonded) to the platform. A dielectrophoretic nanotweezer (DENT), such as, for example, an atomic force microscope (AFM) probe (e.g., a metal-coated silicon AFM probe) can be manipulated to penetrate through the membrane and enter into a single cell. The target mRNA molecules from a single cell is attracted to the probe-end via the dielectrophoretic (DEP) force under the AC (alternating current) field applied by electrodes patterned on the probe. The extracted mRNA can be released for further quantitative/qualitative analysis, and the target cells can be retrieved for the downstream processes.

Using an embodiment of the intergrated platform, single-cellular expression levels of 3 housekeeping genes from HeLa cells were analyzed quantitatively based on the quantification of the extracted mRNAs. To maintain viability of the probed cells, an alternating-current (AC) voltage lower than 1.5 Vpp was applied during mRNA probing. Using an an embodiment of the intergrated platform, in situ mRNA isolation from a mixture of SK-BR-3 and U937 cells was also performed to evaluate various marker-genes' expressions. The mixture of SK-BR-3 and U937 cells was used to mimic a blood sample that underwent primary enrichment of circulating tumor cells (CTCs). The embodiments of the integrated platform described herein combines microfluidic systems' capability of upstream sample processing and downstream multifunctional analysis with non-destructive extraction of mRNA to provide a versatile and powerful tool for biomedical research.

The integrated platform can include an array of microfluidic channels that can efficiently and precisely trap single cells. An external equipment such as an AFM probe, can be inserted into the array, and access a specific cell for further analysis. The integrated platform can perform high throughput single-cell assays. The integrated platform can overcome the limitations of traditional single-cell analysis platforms. Also, mRNA extraction by the AFM probe is sensitive, fast, simple, nondestructive, and does not require cell lysing, or mRNA purification. It targets and non-destructively samples mRNA expression levels down to a few molecules within a single living cell, so that differences between individual cells in a population can be distinguished reliably and sensitively. The integrated platform can provide precise single-cell analysis and diagnostics, the retrieval of cells after analysis, and the monitoring of gene expression within a single cell as a function of time in response to various stimuli. The technique described herein can be used in a wide variety of application areas ranging from systems biology to cancer research.

In some embodiments, a microfluidic device is provided that includes an analysis region and a membrane that seals the analysis region from an ambient environment. The analysis region includes a microfluidic channel configured to trap a microfluidic sample. The membrane is configured to be punctured by a micro-manipulating instrument to form a hole therein to allow the external micro-manipulating instrument to access the microfluidic sample.

The membrane can be configured to be resealable. For example, after the micro-manipulating instrument accesses the microfluidic sample and is removed the membrane closes up and again seals the analysis region from an ambient environment.

A lab-on-a-chip platform can be provided that includes any of the microfluidic device disclosed herein The lab-on-a-chip platform also can include an external micro-manipulating instrument. The external micro-manipulating instrument is configured to analyze a property of the microfluidic sample, such as by incorporating a AFM probe.

In another embodiment, a method of manufacturing a lab-on-a-chip platform is provided. In the method, a microfluidic device is provided. The microfluidic device includes a microfluidic channel and a membrane configured to seal the microfluidic device from an ambient environment. The microfluidic device is sealed, e.g., by coupling the membrane over the microfluidic channel. The microfluidic device is bonded on a substrate. The membrane has a thickness less than 5 µm. The membrane encloses an analysis region of the microfluidic channel.

The microfluidic device preferably is configured with an inlet and an outlet. The inlet and the outlet can be formed through the membrane, such as by using a punch to form the inlet and the outlet through the membrane. The inlet and outlet could be formed in a thicker structure. In one configuration the analysis region is sealed by the thin membrane and the inlet and outlet are upstream (e.g. at a sample processing region) or downstream (e.g., at a post-processing region for post-processing of sample cells after releasing the trapped cells). The inlet and the outlet may be formed by any technique through or may be sealed with a thicker membranes for the purpose of structural integrity and interconnect tightness.

In another embodiment, a method of analyzing a sample is provided. In the method, a microfluidic component is provided. The microfluidic component includes an analysis region that is at least partially enclosed by a membrane. The analysis region has a portion for isolating cells of a sample. The microfluidic component has a sample disposed therein. The sample has cells disposed therein. The membrane is punctured with a tip of a probe of an external micro-manipulating instrument. An individual cell of the sample in the microfluidic channel is manipulated using the tip of the probe.

An embodiment of a microfluidic device described herein integrates a high-efficiency single-cell trapping array configured to trap target living cells injected into the microfluidic devices and a DENT that is configured to extract mRNA from the trapped target living cells. The embodiment of the microfluidic device is capable of measuring mRNA expression levels of each target living cell. The injected cells flow inside one or more microfluidic channels of the embodiments of the microfluidic devices and are trapped individually at a rate of 100 single-cell trappings per 20 s. A modified AFM probe is configured as a DENT. The modified AFM probe is controlled mechanically to penetrate through an ultra-thin polydimethylsiloxane (PDMS) membrane disposed over the microfluidic device to extract mRNA molecules non-destructively from the trapped single target cells. The extracted mRNA molecules then undergo RT-qPCR process to reveal the single-cellular expression levels of target genes in the trapped cells.

In one experimental setup, the embodiment of the microfluidic device trapped 100 live human carcinoma (HeLa) cells in the single-cell trapping array, and the single-cellular expression levels of 3 housekeeping genes, ACTB (beta-actin), GAPDH (glyceraldehyde 3-phosphate dehydrogenase), and HPRT (hypoxanthinephosphoribosyltransferase), were analyzed quantitatively based on the RT-qPCR results of the probed-out mRNA molecules from the trapped single HeLa cells. Microfluidic trapping and in situ single-cell mRNA extraction from a mixture of SK-BR-3 (human breast cancer cell line) and U937 cells (human monocyte cell line) capabilities of the embodiment of the microfluidic device was also evaluated. SK-BR-3 cell line represents a common type of circulating tumor cells (CTCs) found in a patient's peripheral blood, while U937 cell line represents the WBC background of a typical pre-enriched CTC sample. The embodiments of microfluidic devices described herein facilitate the entrapment of single target cancer cells without complicated microfluidic networks, and extract mRNAs from single cells of interest in situ with reduced impact on cell viability from a closed microfluidic environment.

The foregoing method of analyzing can be performed using an external micro-manipulating instrument. In some embodiments, the microfluidic component can be disposed on, under, beside or in an external micro-manipulating instrument that has the probe with the tip.

BRIEF DESCRIPTION OF THE DRAWINGS

FIGS. 3A-3G schematically illustrate a fabrication process of thin membrane covered single-cell trapping array.

FIGS. 4A-1 and 4A-2 illustrate SEM images of the coated AFM probe. FIG. 4A-1 shows the AFM probe after fabrication, with a scale bar of 5 µm and FIG. 4A-2 illustrates a zoom-in image of probe-end, with a sale bar of 200 nm. FIG. 4B is a logarithmic scale color plot showing the simulation result (COMSOL Multiphysics) of the gradient of the electric field square ($\nabla E^2$), once the probe is inserted into the cell with an applied AC field of 1.5 Vpp in amplitude and 10 MHz in frequency.

FIGS. 5A-5D illustrate design principle of the single-cell trapping array. FIG. 5A is a schematic drawing of the three rows of the array with the trajectory of cells. FIG. 5B is a detailed view of the boxed region of FIG. 5A showing cell focusing mechanism. Converging flow (red) and diverging flow (blue) through the dummy traps focus cells towards the traps. FIG. 5C is a detailed view of the boxed region of FIG. 5B describing two major streams that cells experience: delivery flow (Q) and perpendicular flow (q). FIG. 5D is a detailed view of the boxed region of FIG. 5C demonstrating the geometry of a single trap.

FIG. 7A is a perspective view of a microfluidic single-cell trapping unit of the single-cell trapping array. FIG. 7B is a side view of the microfluidic single-cell trapping unit of the single-cell trapping array.

FIG. 15A illustrates the calculated absolute numbers of extracted mRNAs for applied voltages at 1.1 Vpp, 1.5 Vpp and 1.9 Vpp based on the above Ct values of the RT-qPCR experiment and standard curves.

FIGS. 15B-1 to 15B-8 illustrate bright-field and fluorescence microscopic images of mRNA-extracted cells stained with Calcein AM after on-chip culturing for 12 h.

DETAILED DESCRIPTION OF THE PREFERRED EMBODIMENT

Figures 1, 1A:
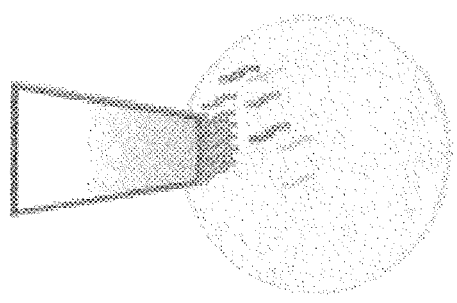
Figure 1A:
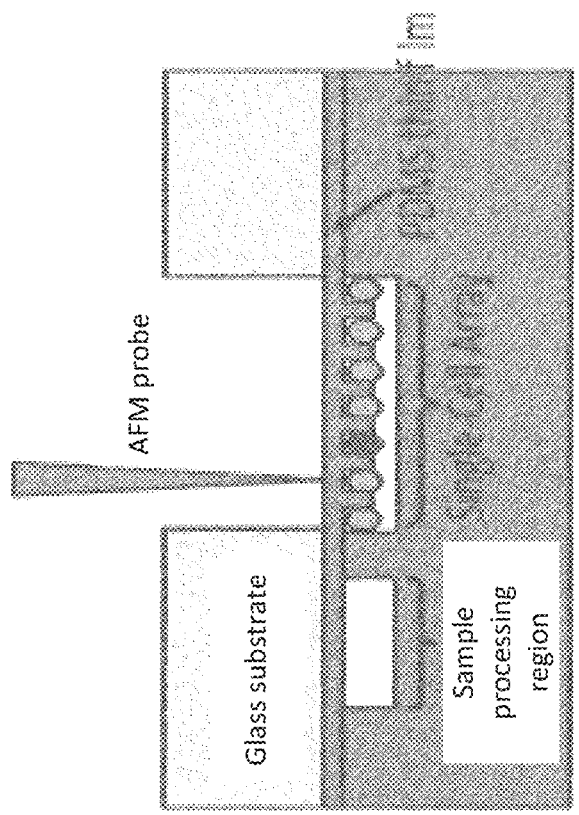
FIG. 1A illustrates a schematic overview of an embodiment of an integrated device. The device is capable to sequentially and deterministically trap one hundred cells in twenty seconds with a single-cell loading efficiency of 95%. After the cells are trapped in the single-cell array, a modified AFM probe can penetrate through the membrane and extract intra-cellular molecules (e.g. mRNAs) from a single cell as shown in FIG. 1A-1. The extracted molecules can be released for further quantitative or qualitative analysis, and the cells can be released for downstream processes.
Figure 1B:
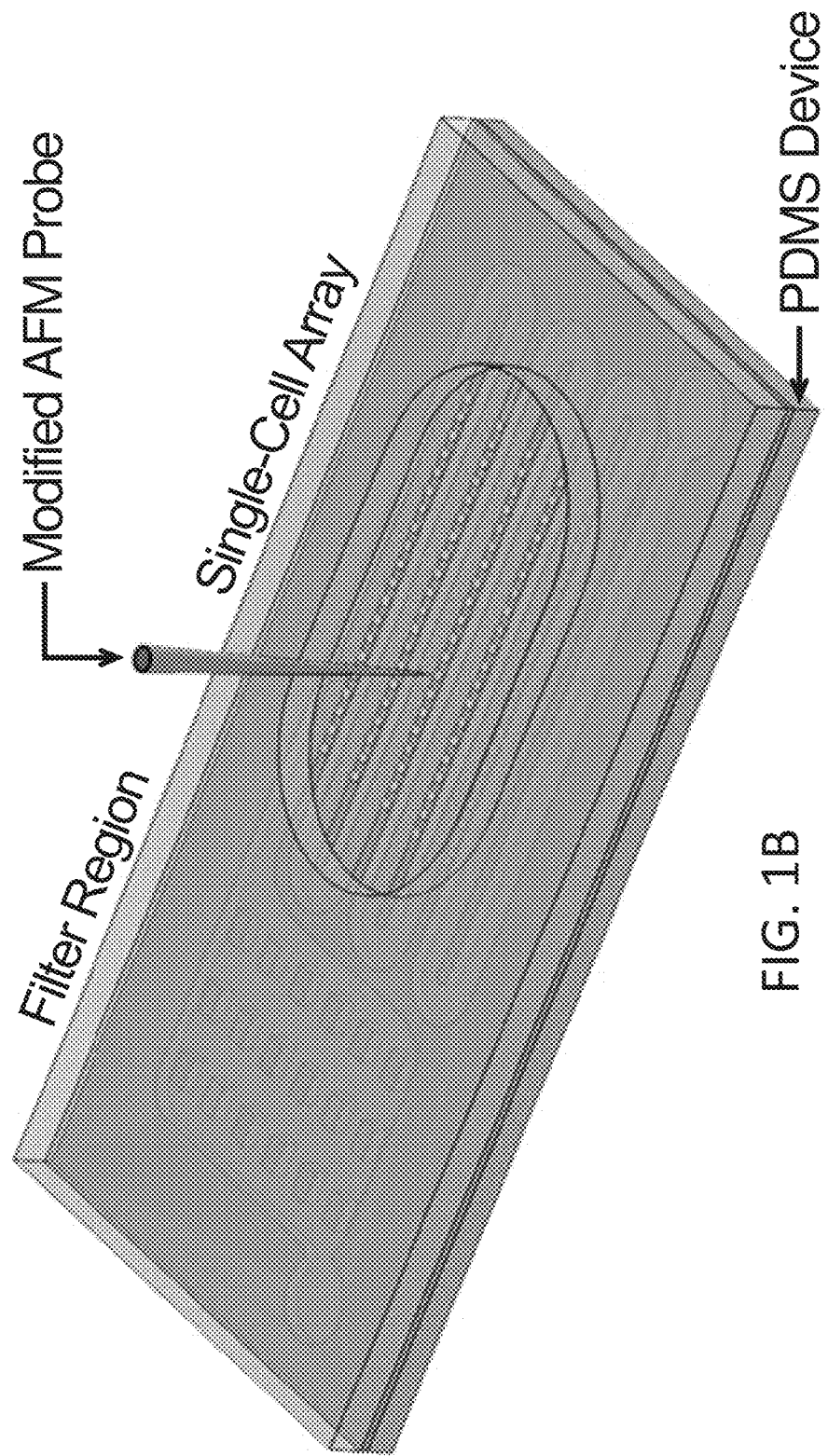
FIG. 1B illustrates a perspective view of an embodiment of an integrated microfluidic device comprising a single cell trapping array encapsulated by a PDMS membrane and a DENT configured to penetrate through the PDMS membrane.

Various embodiments disclosed herein comprise a microfluidic lab-on-a-chip platform for high throughput single-cell trapping, integrated with a modified AFM probing system for the extraction of intracellular molecules (e.g. mRNAs, proteins, small molecules) from an individual living cell. The overall schematic design of an embodiment of a microfluidic lab-on-a-chip platform is illustrated in FIG. 1A. FIG. 1B illustrates a perspective view of an embodiment of an integrated microfluidic device comprising a single cell trapping array encapsulated by a PDMS membrane and a DENT configured to penetrate through the PDMS membrane. Some of the features of the various embodiments disclosed herein are listed as below:

The single-cell trapping array sealed with an ultra-thin PDMS membrane facilitates an external micro-manipulating instrument (e.g. AFM probes, micro-injectors, DENT) to penetrate through the membrane and access a trapped single cell for probing of mRNA expression levels as shown in FIGS. 1A and 1A-1.

The single cell trapping array can be integrated downstream from a microfluidic sample sorting and separation device, enabling the pre-concentration of targeted cells that are probed further for molecular markers.

The modified AFM probe is able to extract intracellular molecules from a single cell by dielectrophoresis (DEP), and the extracted biomolecules can be released for further analysis.

The AFM-based intracellular molecule extraction is sensitive, fast, simple, nondestructive, and does not require cell lysing.

The probed cells can be retrieved from the trapping sites inside the microfluidic device for downstream study.

Various embodiments of the platform discussed herein enable precise analysis and measurement of the genomic information of single cells, such as monitoring the gene expression level within a single cells as a function of time in response to various external stimuli. The techniques described herein can be useful for different applications from systems biology to cancer research.

Microfluidic Chip Fabrication

The microfluidic device comprises a sample processing region (e.g., configured to perform sample filtering, sample focusing, sample sorting, etc.) and a single-cell trapping channel. It can comprise a variety of materials such as polymers, plastics, glasses, and so on. As a prototype, a PDMS based microfluidic device was fabricated using standard soft-lithography method with an SU8 master mold on a silicon substrate. Degassed PDMS pre-polymer mixture (mixed PDMS base with curing agent in a 10 to 1 ratio, Sylgard 184, Dow Corning Inc.) was cast over the mold and baked at 65° C. overnight. The cured PDMS with embedded channels was subsequently diced by scalpel and removed from the master mold. One inlet and one outlet were punched through the PDMS slab by a 1.5 mm hole-puncher, and then the PDMS slab was ready to be bonded with the PDMS membrane by oxygen plasma treatment.

Another prototype microfluidic device was fabricated in PDMS by soft lithography method. The microfluidic device comprises a filter region and a serpentine-shape single-cell trapping channel. A master mold was produced by patterning SU-8 photoresist manufactured by MicroChem on a silicon wafer using standard two-layer photolithography. Liquid PDMS mixed with a curing agent (ratio of 10:1) was cast on the mold and cured for 3 h in a convection oven at 65° C. for complete cross-linking. The PDMS microchannel was then irreversibly sealed with an ultra-thin PDMS membrane after exposure to oxygen plasma for 60 s.

Spin Coating of the Ultra-Thin PDMS Membrane

Figure 2:
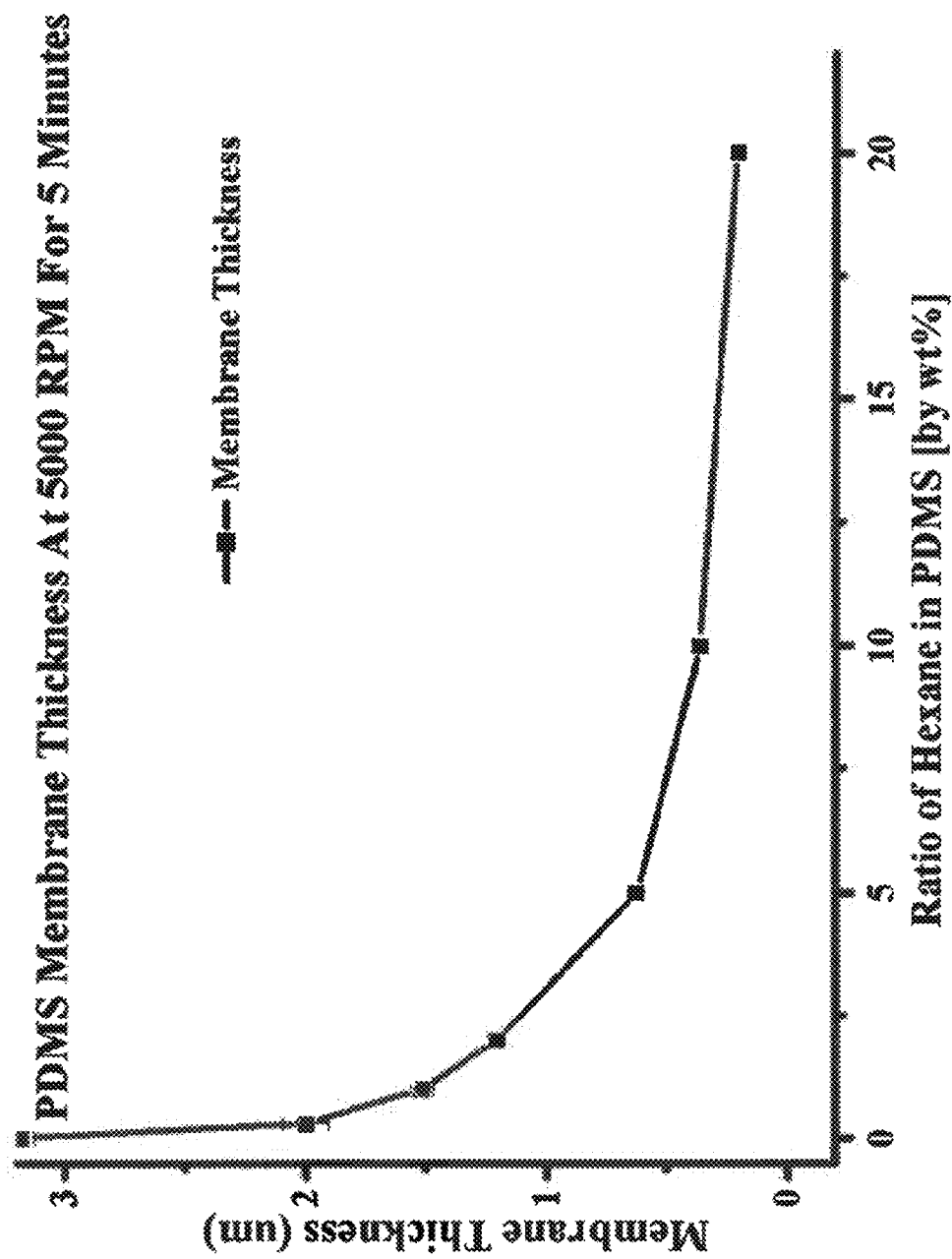
FIG. 2 illustrates a graph of PDMS membrane thickness and PDMS to Hexane dilution ratio.

The ultra-thin PDMS membrane was fabricated by spin coating the PDMS material on a silicon wafer and peeling off the coated PDMS layer after curing. In some methods, a low index Teflon® amorphous fluoroplastic (AF) resin in solution (e.g., 400S2-100-1 manufactured by Dupont) diluted in Fluorinert™ FC-40 manufactured by Acros Organics by a 1:5 ratio can be spin-coated on the silicon wafer, and cured by baking at 120° C. for 10 min before spin-coating the ultra-thin PDMS membrane. Diluted Teflon® AF solution coated on the silicon wafer can function as an adhesion-reduction layer to facilitate the easy peeling off of the ultra-thin PDMS membrane and/or reducing the risk of breakage of the ultra-thin PDMS membrane when peeled off from the silicon wafer. An ultra-thin PDMS membrane with a thickness of 1 μm was fabricated by diluting a PDMS pre-polymer mixture in hexane (Sigma-Aldrich, St. Louis) with a weight ratio of 1:2 to decrease its viscosity and spin coating the diluted PDMS pre-polymer mixture on a Teflon® coated silicon wafer at 5000 rpm for 5 min. Diluting PDMS pre-polymer mixture in hexane reduced its viscosity; therefore a much thinner membrane could be fabricated at similar spin coating parameters. The coated PDMS membrane was baked at 120° C. for 45 min to evaporate the hexane, and at 65° C. overnight or for 1 day for curing. FIG. 2 shows the thickness of PDMS membranes having different PDMS to hexane ratios at same spin coating conditions, i.e. 5000 rpm for 5 min.

Chip Assembly

The device assembly procedure is illustrated in FIGS. 3E-3G. Bond-detach lithography was used to seal the microfluidic channel imbedded PDMS slab with the ultra-thin PDMS membrane. The sealed device was then bonded to a glass slide post oxygen plasma treatment. The glass slide has a through-hole in the single-cell trapping array region for the penetration of an AFM probe. A plastic tube was inserted through the inlet port for the input of cell suspensions.

Fabrication of the Modified AFM Probe

Scanning Electronic Microscopy (SEM) images of the modified AFM probe are shown in FIGS. 4A-1 and 4A-2. The probe was fabricated based on a commercially available conical, highly doped (resistivity 4 to 6 ohm-cm, k-45 N/m) silicon AFM probe (Applied Nanotech, Inc., U.S.) having a length of 15 μm. The fabrication process comprises growing a 20-50 nm (e.g., 40 nm) thick layer of $SiO_2$ on the AFM probe in a conventional oxidation furnace. The $SiO_2$ layer served to electrically insulate the entire silicon probe including the AFM cantilever. Then a 10 nm thick chromium adhesion layer followed by a 20 nm thick gold layer were deposited on top of the $SiO_2$ layer by ion-beam sputtering to serve as the outer electrode. After deposition of the metal layers, the end of the gold coated tip was cut using focused ion beam (FIB) to expose the inner silicon core having a width of 300 nm. In some methods of fabrication, the gold coated tip can be polished by a flat $Si_3N_4$ wafer, so that the probe end was cut carefully, and the inner-doped silicon core was exposed. The exposed inner-doped silicon core can be configured to form the second electrode for dielectrophoresis (DEP).

In another embodiment, the modified AFM probe can be a highly doped silicon probe coated with a 20 nm $SiO_2$ electrical insulation layer and a 10 nm/30 nm Cr/Au outer electrode, with its end cut so that the silicon core (inner electrode) is exposed.

Principle of Intra-Cellular Molecule Extraction Using a Modified AFM Probe

The modified AFM probe can be regarded as a dielectrophoretic nanotweezer (DENT). Application of an AC (alternating current) electric field between the inner (silicon core) and outer electrodes (Cr/Au nano-layer) of the AFM probe creates a large electric field gradient, resulting in a dielectrophoretic force strong enough to attract molecules (e.g. mRNAs, proteins, small molecules) to the probe-end. The DEP force is given by the equation $F_{DEP}=[(V\alpha)/2]\nabla|E|^2$, where V is the particle volume and α is the polarizability. In an embodiment, AC voltage of 1.5 Vpp at 10 MHz was applied to the modified AFM probe-end and inserted into a target cell. Logarithmic scale color plot showing the simulation result (COMSOL Multiphysics) of the gradient of the electric field square ($\nabla E^2$), once the probe is inserted into the cell with an applied AC field of 1.5 Vpp in amplitude and 10 MHz in frequency is shown in FIG. 4B. The largest $\nabla E^2$ of approximately $10^{24}$ $V^2/m^3$, was distributed in the oxide part in between the inner core and the outer electrode. The modified AFM probe-end was removed from the cell after approximately 60-75 seconds and the AC field was turned off. In various embodiments, selective mRNA extraction can be achieved by coating the probe with the oligonucleotide primers hybridizing to the target mRNA. After the AC electric field application, all the mRNAs move toward the probe-end, but only target mRNA molecules hybridize to the oligonucleotide primers. After hybridization, the probe is withdrawn from the cell and the AC field can be tuned off.

Details of an Experimental Test Set-up

An experimental set-up was used to test the capabilities of the microfluidic device and the modified AFM probe to extract mRNA molecules from a single cell. The fabricated AFM probe was mounted on a probe-holder with electrical connection for mRNA extraction. The inner Si core was connected to silver paint provided at the bottom of the holder, and the outer Au layer was connected to a thin piece of copper electrode on top of the holder via a spring contact. This copper electrode was connected with the AC power supply, and it helped to fasten the AFM probe. The experimental set-up further comprised an inverted microscope (e.g., Olympus IX71) with a CCD camera (Photometrics), equipped with an add-on upright imaging system comprising a 40× lens tube with motorized zoom/focus function and a USB camera (Thorlabs). A 3D-printed microfluidic chip holder was attached to the motorized x-y translation stage (Thorlabs) with a calculated moving resolution of 200 nm in x-y plane. The probe-holder was controlled by a stepper motor (Thorlabs) with a calculated moving resolution of 50 nm in z direction for penetration. A LabVIEW controlled graphic user interface was developed to facilitate operation of the set-up.

High electric field gradient ($\nabla E^2$) can be required in some experiments because of the effect of the complex composition of cytoplasm on the polarizability of mRNA molecules inside the cell. The strength of the DEP force can also be damped from the probe-end, causing mRNA molecules to move from cytosol to the probe-end due to the positive DEP effect. If the applied AC voltage were high enough, the entire cytosol volume could be subjected to a DEP force strong enough to drive mRNA molecule movement, so all mRNA molecules in the cytosol could be concentrated at the probe-end. However, high AC voltage could affect the viability of some cells after mRNA extraction.

Cell Culture and Viability Assay

To test the capabilities of the microfluidic device and the modified AFM probe samples comprising HeLa cells, SK-BR-3 cells and/or U937 cells were used. HeLa cells (American Type Culture Collection, ATCC) were cultured in DMEM medium (Gibco) supplemented with 10% fetal bovine serum (FBS, Gibco) and 1% penicillin/streptomycin (1000 U/mL, Gibco). SK-BR-3 cells (ATCC) were cultured in McCoy's 5A medium (ATCC) supplemented with 10% FBS and 1% penicillin/streptomycin. U937 cells (ATCC) were cultured in RPMI 1640 medium (Gibco) with 10% FBS and 1% penicillin/streptomycin. Cells were passaged every 3-4 days following standard protocols and cultured in a humidified incubator at 37° C. with 5% $CO_2$. The samples were flowed through the microfluidic device and individual cells in the samples were trapped in the single-cell trapping array. The trapped individual cells were probed by the modified AFM probe to extract mRNA molecules. To validate the viability of the mRNA-extracted cells after probing, a live assay was performed by flowing 2 μM Calcein AM (Sigma-Aldrich) through the microfluidic trapping array for 15 min after 12 h on-chip culturing of the probed cells, and measuring the green fluorescence intensity.

Primer Design

The mRNA sequences of ACTB, GAPDH, HPRT, CD45, EpCAM and HER2 were checked in GenBank, and their primers were designed using the online PrimerQuest® Tool (Integrated DNA Technologies). All the primers were designed to be intron-spanning to preclude amplification of genomic DNA. The sequences of the above primers were as follows: ACTB, 5'-TCATCACCATTGGCAATGAG-3' (SEQ ID NO: 1, forward) and 5'-ACTCCATGCCCAG-GAAGGA-3' (SEQ ID NO: 2, reverse); GAPDH, 5'-TC-CACTGGCGTCTTCACC-3' (SEQ ID NO: 3, forward) and 5'-GGCAGAGATGATGACCCTTTT-3' (SEQ ID NO: 4, reverse); HPRT, 5'-TGACCTTGATTTATTTTGCATACC-3' (SEQ ID NO: 5, forward) and 5'-CGAGCAAGACGTTCA-GTCCT-3' (SEQ ID NO: 6, reverse); CD45, 5'-CGGCT-GACTTCCAGATATGAC-3' (SEQ ID NO: 7, forward) and 5'-GCTTTGCCCTGTCACAAATAC-3' (SEQ ID NO: 8, reverse); EpCAM, 5'-CGCAGCTCAGGAAGAATGTG-3' (SEQ ID NO: 9, forward) and 5'-TGAAGTACACTGGCAT-TGACG-3' (SEQ ID NO: 10, reverse); and HER2,5'-AAAGGCCCAAGACTCTCTCC-3' (SEQ ID NO: 11, forward) and 5'-CAAGTACTCGGGGTTCTCCA-3' (SEQ ID NO: 12, reverse).

All the primers were purchased from Integrated DNA Technologies. DNA oligomers (Integrated DNA Technologies) with same sequences as the target genes' amplicons were used to construct standard curves for the calibration of molecule numbers from RT-qPCR results.

Protocols of Reverse-Transcription—Quantitative Polymerase Chain Reaction (RT-qPCR)

In one method of testing, the AFM probes with target mRNA molecules were dropped into PCR tubes containing 5 μL distilled water. The mRNA molecules extracted from cell lysing RNA extraction kit (ISOLATE II RNA Mini Kit, BioLine Ltd., London, UK) were diluted into a concentration of 10 cells RNA molecules per 5 μL water, and put into PCR tubes on ice. The iScript cDNA Synthesis Kit (Bio-RAD, Hercules, Calif., USA) was used to make cDNAs (complementary deoxyribonucleic acids) from the isolated mRNA molecules following the kit protocols. Thereafter, 10% the cDNA products was used to perform real-time qPCR analysis. For real-time qPCR cycling, SYBR green (Thermo Fisher Scientific) was used as the probe in the Chromo4 qPCR system from Bio-RAD, and the following thermal cycling protocol was used: 45 cycles of 94° C. for 15 s, 57° C. for 30 s and 72° C. for 45 s for each mRNA samples.

In another method of testing, after single-cell mRNA probing, the extracted mRNA molecules were released from the tip-end of the AFM probe into PCR tubes containing reverse transcriptase assays. Reverse transcription was carried out to generate complementary DNAs (cDNAs) using the iScript™ cDNA Synthesis Kit (Bio-Rad). Thereafter, for the qPCR analysis of each target gene, 10% of the total cDNA product from a single cell was transferred into a PCR tube as suggested in the manufacturer's protocol. For real-time qPCR cycling, SYBR® Green (Bioline) was used as the reporter dye in the Chromo4 qPCR instrument (Bio-Rad). The following thermal cycling protocol was used: 45 cycles of 94° C. for 10 s, 58° C. for 10 s and 72° C. for 20 s. The melting curves were generated by increasing the temperature from 60° C. to 95° C. and holding for 10 s after each 0.2° C. temperature increment. As for the positive controls, mRNAs extracted from bulk cell lysates using the cell-lysing RNA extraction kit (ISOLATE II RNA Mini Kit, Bioline) were diluted to a concentration of 10 cells' mRNA molecules per 5 μL distilled water, and were quantified following the same RTqPCR process as mentioned above. Synthetic oligomers with the sequences of target genes' amplicons were diluted in series as templates to generate standard curves for data calibration.

Design of the Single-cell Trapping Array

Some embodiments of the microfluidic device can comprise an array of micro-wells that are configured to trap individual cells in the sample. Examples of the microfluidic devices comprising array of micro-wells are described in U.S. Publication No. 2017/0107507 which is incorporated by reference herein in its entirety for all that it discloses.

Some other embodiments of the microfluidic device can comprise a serpentine cell delivery channel with grooves arrayed along the channel edge. FIG. 5A illustrates such an embodiment of a trapping array. FIG. 5A is a schematic drawing of the three rows of the array with the trajectory of cells. The trapping array is based on a design schematically illustrated in FIG. 6 which is a 5-row serpentine channel with 20 grooves arrayed along the channel edge of each row.

Figure 6:
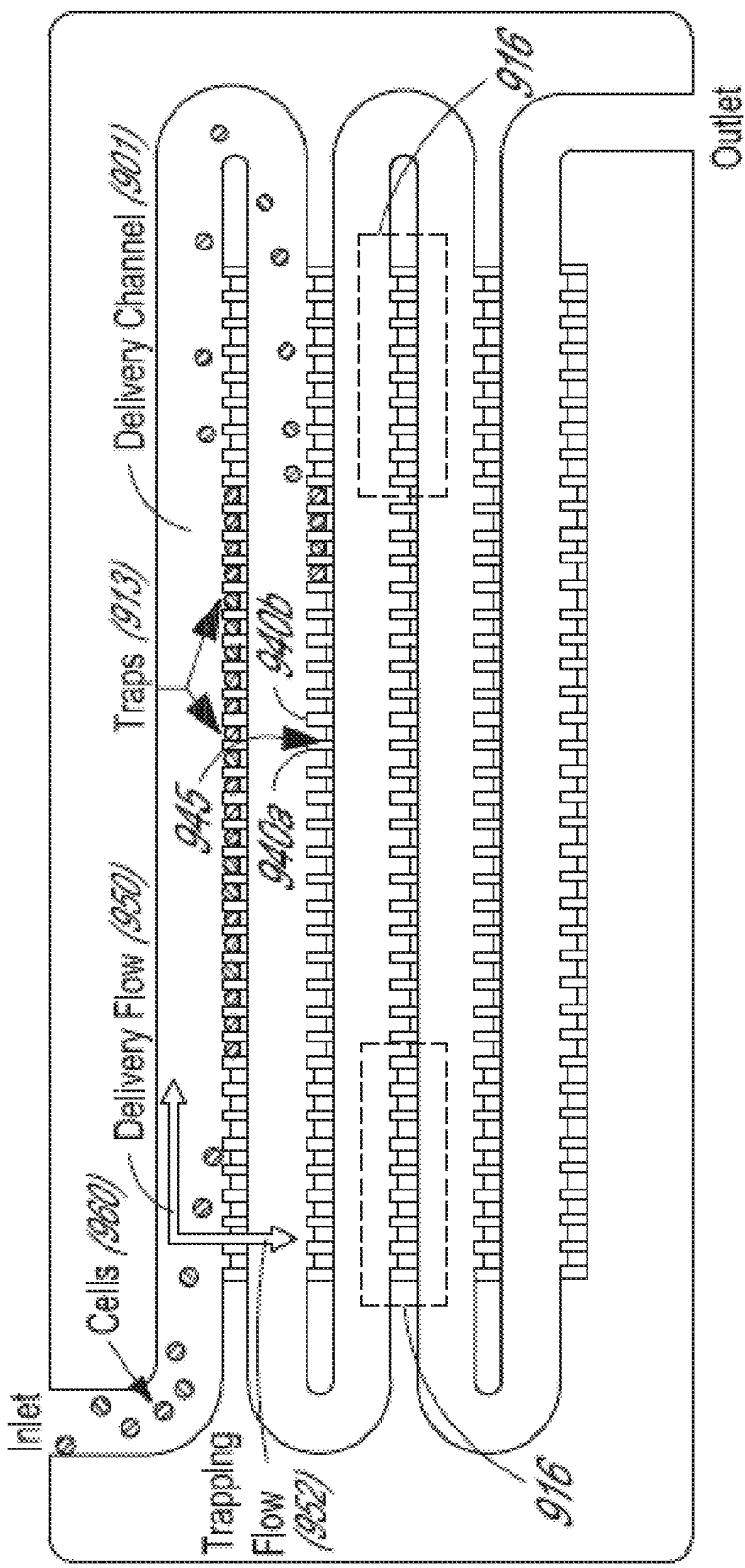
FIG. 6 illustrates an embodiment of a serpentine microfluidic channel that comprises a single-cell trapping array.

The trapping array 900 shown in FIGS. 5A and 6 comprises a serpentine cell delivery microfluidic channel 901 with an array of trapping units 913 disposed along an edge of the channel 901. The serpentine delivery channel includes a plurality of turning zones such that the trapping units of the trapping array 900 are arranged in a plurality of rows. The trapping array 900 includes a plurality of dummy traps 916 disposed at the turning zones of the channel 901. The dummy traps 916 are configured to focus cells towards the trapping units 913. Each trapping unit 913 includes a groove (e.g., a rectangular groove) 945 disposed between two support structures 940a and 940b. The geometry of each trapping unit 913 is schematically illustrated in FIG. 7A, FIG. 7B and FIG. 5D. In various embodiments of the trapping unit 913, the groove 945 can include a ledge 947 to receive and trap an individual cell as depicted in FIG. 7A and FIG. 5D. As noted from FIG. 5D, for various embodiments of the trapping unit 913, the height of the trap ($h_T$) is smaller than the height of the delivery channel (H), generating a gap area ($h_G$=H–$h_T$). FIG. 5B corresponds to the boxed region 910 in FIG. 5A showing cell focusing mechanism. FIG. 5C corresponds to the boxed region 920 in FIG. 5B. FIG. 5D corresponds to the boxed region 925 in FIG. 5C.

The trapping principle relies on the two hydrodynamic flows—horizontal delivery flow and perpendicular trapping flow. While cells are delivered to the traps sequentially by the horizontal delivery flow, there is a perpendicular stream flowing through the gap area at each trapping unit, crossing each row of the delivery channel and pushing cells into traps. To ensure that only one cell is trapped at each trapping unit, the width (w) and the length ($L_T$) of each trap is the same as target cell diameter, so that once a cell occupies a trap, it physically excludes another cell from trapping at the same spot. At the turning zone of each row, there are dummy traps with $L_T$ smaller than cell diameter, which do not trap cells but help generate perpendicular flow for cell focusing.

In accordance with the trapping principle, as depicted in FIG. 5B when the cells flowing through the serpentine delivery channel 901 are turned by the turning zones, they experience a converging flow as depicted by red arrows in FIG. 5B and a diverging flow as depicted by the dashed line in FIG. 5B. The flow pattern along the dummy traps of the turning zone 916 focus cells towards the trapping units 913. As depicted in FIG. 5C, the cells flowing through the channel 901 in the vicinity of the trapping units 913 experience two flow streams: a delivery flow (Q) and a perpendicular flow (q). The delivery flow (Q) is depicted as delivery flow 950 in FIG. 6 and the perpendicular flow (q) is depicted as perpendicular flow 952 in FIG. 6.

Referring to FIG. 6 and FIG. 5B, the perpendicular stream 952 is directed along the width of serpentine channel 901 and can cause the cells to cross each row of the delivery channel 901 and be pushed to into various trapping units 913 as depicted in FIG. 5C. The dummy traps 916 at the turning zone of each row can help generate perpendicular flow to focus cells towards the traps as depicted in FIG. 5B. Accordingly, in the embodiment illustrated in FIGS. 5A and 6, cells are delivered to the individual trapping units 913 sequentially by the horizontal delivery flow 950, and pushed into the traps by the perpendicular pushing flow 952. Since the trap size is similar to the cell size, when a cell occupies a trap, it physically excludes the next cell and reduces the possibility of trapping multiple cells. In an embodiment of a microfluidic device, in order to trap 100 single cells sequentially, the delivery channel can be configured as a 5-row format, with 20 traps in the middle of each row, and dummy focusing traps in the beginning and end of each row.

Figure 8A:
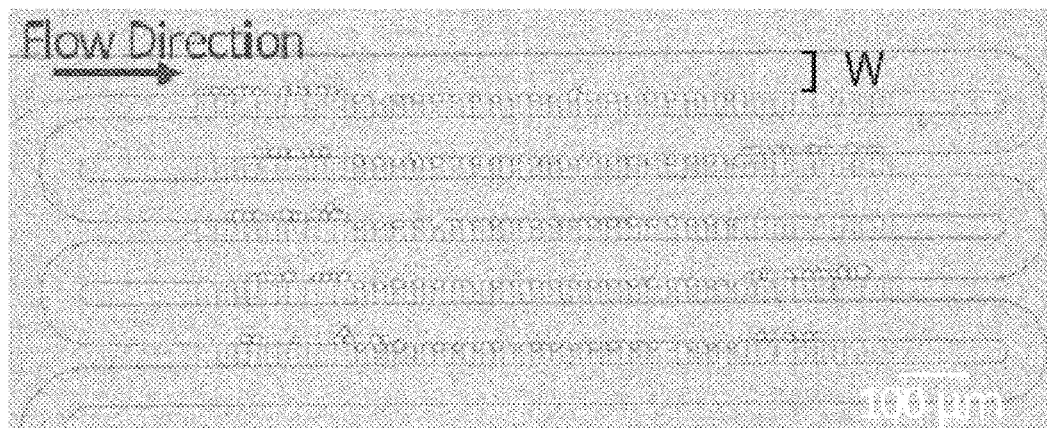
FIG. 8A illustrates an example of a trapping array.
Figure 8B:
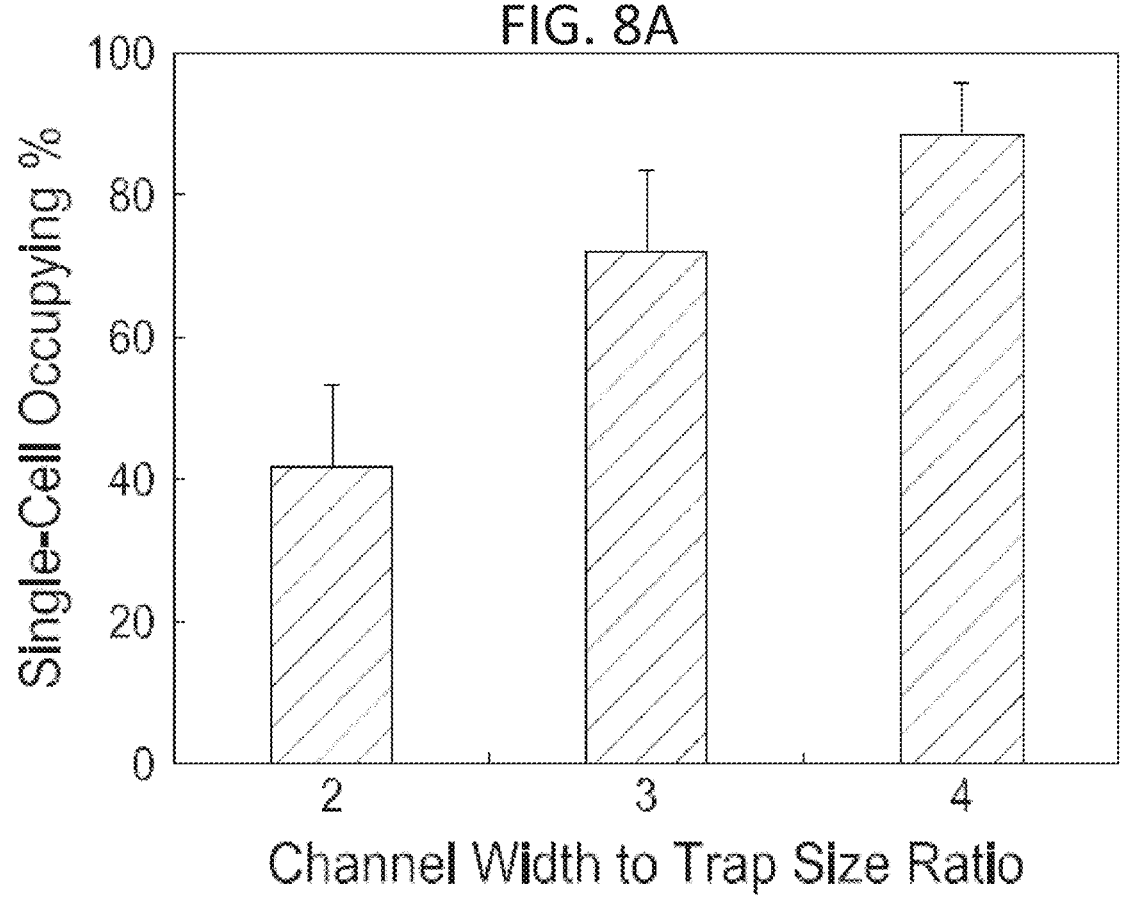
FIG. 8B illustrates the dependence of the percentage of single-cell occupancy in a trapping array to the ratio of channel width (W) to trap size ($W_T$).

It was found that the trapping efficiency which is related to the percentage of single cell occupancy does not depend on flow rate, but instead depends on the resistance ratio between horizontal delivery flow and perpendicular trapping flow, which in turn depends on the geometry of the trapping array. For example, the ratio of main channel width to trap size can be modified to vary the trapping efficiency. With every other parameter kept consistent, the main channel width, W can influence resistance ratio between horizontal delivery flow and perpendicular trapping flow. For example, when a width (W) of the main channel is less than a threshold width (Wthr), the delivery flow may be too strong resulting in empty traps. When a width (W) of the main channel is greater than a threshold width (Wthr), the delivery flow may not be strong enough compared to the perpendicular flow resulting in multiple cells clogging at one trapping unit. The threshold width (Wthr) can be about four times the diameter of the cells to be trapped. In some embodiments, a 4:1 ratio between the main channel width (W) and trap size may be sufficient to achieve high trapping efficiency (e.g., greater than 80%) as depicted in FIG. 8B.

Accordingly, the trapping efficiency can be modified by modifying the design parameters of the trapping array. Thus, embodiments of a microfluidic device comprising a trapping array designed in accordance with the principles discussed above can be adaptable to a wide range of the input flow rates, and can be easily integrated with other microfluidic components. As all the parameters of this single-cell trapping array can be scaled up and down relative to the target cell diameter, therefore, this single-cell trapping design is adaptable for isolation cells with arbitrary diameters individually.

Single-Cell mRNA Extraction by a Modified AFM Probe

Figures 9A, 9B, 9C, 9D:
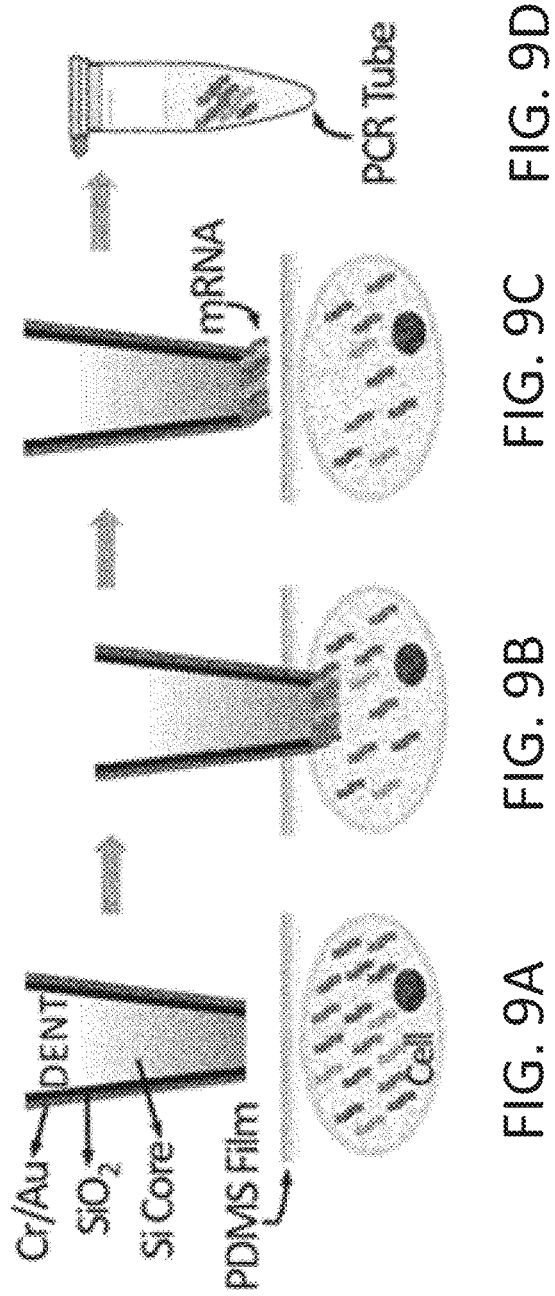
FIGS. 9A-9D illustrate a mechanism of the single-cell molecule-extraction using DENT. Application of AC field between the inner Si core and the outer metal layer of the DENT creates a large electric field gradient at the probe-end, generating a dielectrophoretic attractive force to attract mRNA molecules toward the probe-end as shown in FIG. 9B. The probe is then retracted from the device as shown in FIG. 9C, and mRNA molecules are released from the tip to perform RT-qPCR for quantitative gene expression analysis as shown in FIG. 9D.

After individual cells are trapped in the single-cell trapping array, the modified AFM probe penetrates through membrane and enters into a specific cell controlled by a micro motor. The principle of intra-cellular molecule extraction is described in FIGS. 9A-9D. As described above, the modified AFM probe can be regarded as a dielectrophoretic nanotweezer (DENT). Application of an AC (alternating current) electric field between the inner (silicon core) and outer electrodes (Cr/Au nano-layer) of the probe creates a large electric field gradient ($\nabla E^2$), resulting in a dielectrophoretic force, $F_{DEP}$ described above, strong enough to attract molecules (e.g. mRNAs, proteins, small molecules) to the probe-end. As illustrated in FIG. 9B, the fluorescent molecules are attracted to the probe-end. FIGS. 9A-9D explains the procedure of the selective mRNA extraction. This is achieved by decorating the probe with the oligonucleotide primers hybridizing to the target mRNA. After the AC electric field application, all the mRNAs move toward the probe-end, but only target mRNA molecules hybridize to the oligonucleotide primers as shown in FIG. 9B. After hybridization, the probe is withdrawn from the cell and the AC field is tuned off as shown in FIG. 9C. The target mRNA molecules can then be released to perform RT-qPCR as shown in FIG. 9D. The AFM probe can be configured to penetrate through the membrane and access another cell trapped in a different portion of the single cell trapping array during or after the contents of the specific cell are being analyzed.

Experiment Results of Single-Cell Trapping

Figure 10:
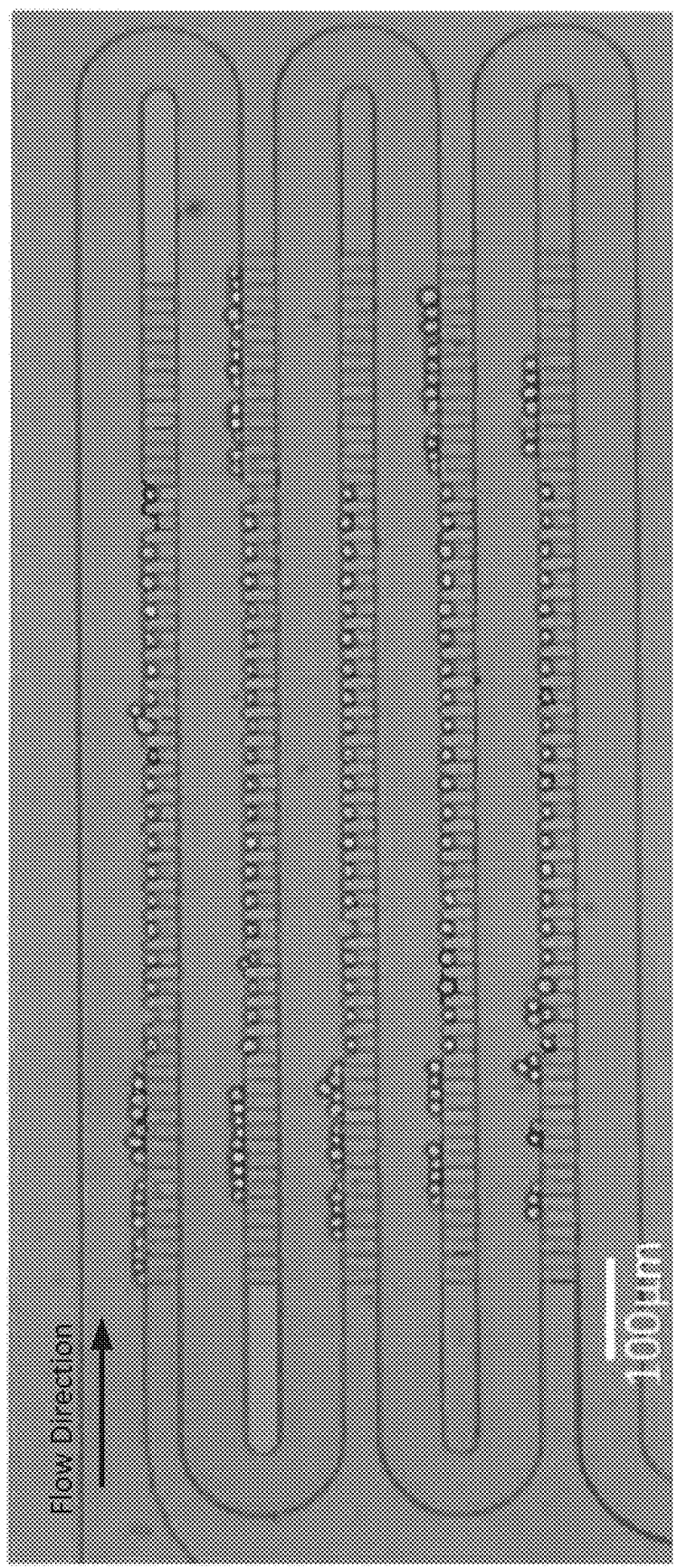
FIG. 10 is a bright-field image of trapping about 100 single HeLa cells within the ultra-thin PDMS membrane-sealed single-cell array. The trapping array has a single-cell occupancy of about 97%.

For initial proof of concept, an embodiment of a microfluidic device comprising a single-cell trapping array illustrated in FIG. 6 was used to trap HeLa cells to investigate device trapping efficiency as well as the feasibility of gene-expression profiling for trapped target cells. The trapping efficiency of the designed device was tested using HeLa cells with a diameter of around 15 μm. Different channel design parameters were tested experimentally, and the trapping result with the optimized parameter is shown in FIG. 10. Up to 98% single-cell occupying efficiency was achieved, with an average single-cell occupying efficiency of 94%±4%. For the optimized design, the trap width ($W_T$) was set to be 15 μm (similar to the target cell diameter), the delivery channel height (H) was 18 μm, the gap height ($h_G$) was 4 μm, and the delivery channel width ($W_T$) was 60 μm (four times of the target cell diameter). HeLa cell concentration was $1 \times 10^6$/ml, the experimental flow rate was 2 μL/min, and the entire trapping process was achieved within less than 1 minute.

Experiment results also showed that the trapping efficiency was independent from the input flow rate, but was controlled by the resistance ratio between the horizontal delivery flow and the perpendicular pushing flow, which was directly determined by the design geometry. This indicates that the trapping device is adaptable to a wide range of the input flow rate, and can be easily integrated with other microfluidic components. As all the parameters of this single-cell trapping array can be scaled up and down regarding to the target cell diameter, therefore, this single-cell trapping design is adaptable for isolation cells with arbitrary diameters individually.

Experiment Results of Single-cell mRNA Probing

Figure 11C:
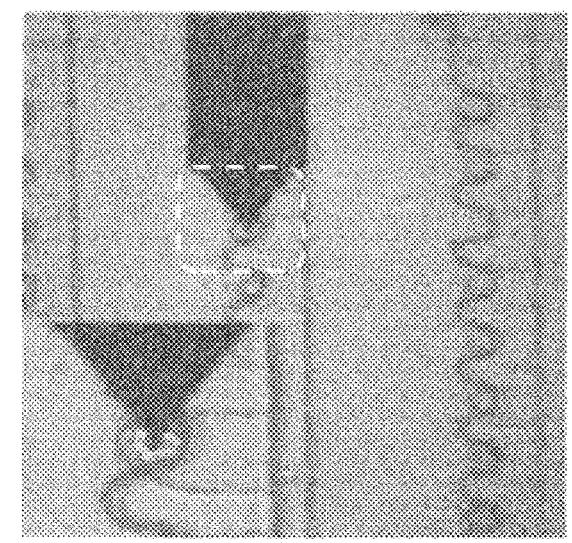
FIGS. 11A-11C illustrate captured microscopic images of the selective mRNA extraction from the single HeLa cell using an AFM probe penetration. White box indicates the cell of interest
Figure 11B:
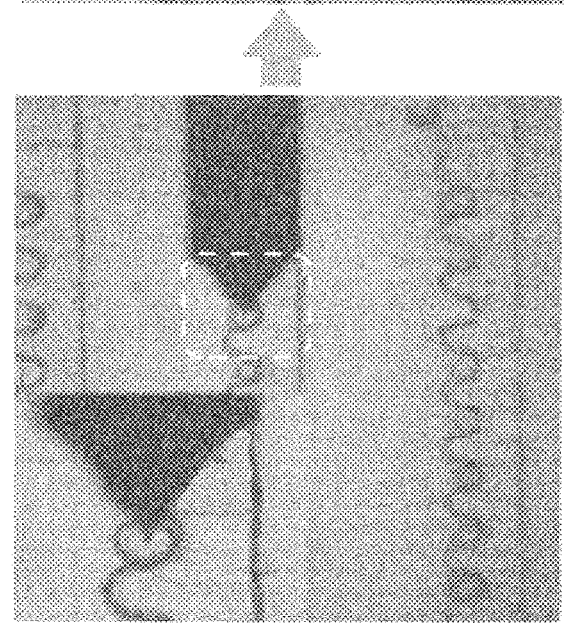
Figure 11A:
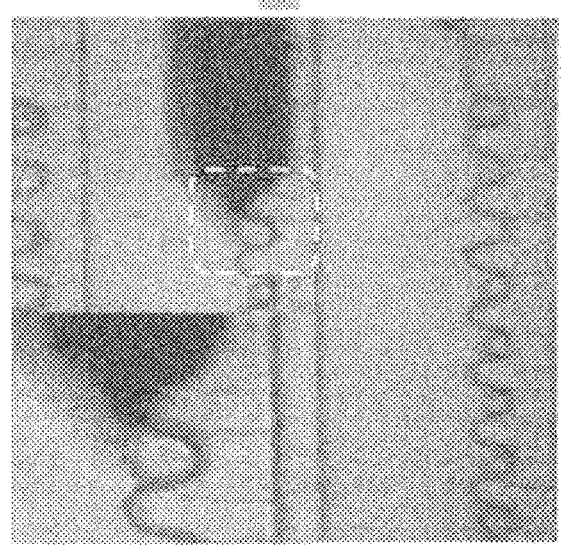

The bright-field microscopic images representing the procedure of single-cell mRNA extraction using the AFM probe are shown in FIGS. 11A-11C. The microfluidic device was placed under an upright microscope and on top a motorized chip-holding stage, and was moved in x-y plane to align a target cell with the tip-end of the modified AFM probe. The probe was controlled to move down along z direction until the contact between the tip-end and the PDMS film led to localized membrane deformation, with wrinkles near the tip-end observed under the microscope. Short AC pulses were then applied to the stepper motor to move the probe further down (along z direction) in 500-nm pulse-steps for penetration. As the target cell was in close contact with the PDMS film, and the cell membrane thickness was less than 10 nm, once punched through the PDMS film, the AFM probe would penetrate through the cell membrane and insert into the cytoplasm. The penetration of the AFM probe was stopped when the probe punched through both the PDMS sealing film and the cell membrane, which could be indicated by a clear relaxation of the cantilever bending. The interface between the probe and the PDMS membrane can be easily observed by the membrane deformation under microscope in FIGS. 11A-11C. Once the probe inserted into the cell, the AC field between inner and outer electrodes was turned on, and mRNA molecules were attracted toward the tip-end by DEP force.

Figure 12A:
FIG. 12A illustrates fluorescent image of the DENT probe before penetration into a Calcein AM-stained HeLa cell.
Figure 12B:
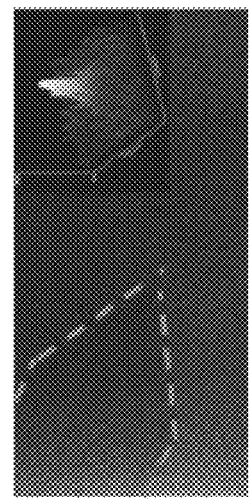
FIG. 12B illustrates fluorescent image of the DENT probe after penetration into a Calcein AM-stained HeLa cell, with a 5 μm×5 μm fluorescence intensity plot of the probe-end on the right corner.

Upon the application of AC field to the inner and outer electrodes of the AFM probe, mRNA molecules within the cell were attracted toward the probe-end by dielectrophoresis effect wherein the AC voltage of 1.5 $V_{pp}$ at 10 MHz was applied to the probe-end. After 60~75 seconds, the probe was removed from the cell and the AC field was turned off. The extracted mRNA molecules were then released and quantified by RT-qPCR to obtain the cell's gene expression fingerprint. The self-sealing capability of the ultra-thin PDMS film was such that no punctured hole or leakage was observed under the microscope after retracting the probe from the cell-trapping array. Also, there was no leakage when cell staining solution or PBS buffer was pumped into the single-cell array after probing, at the flow rate of 2 μL/min for several hours. To verify that the tip was inserted into the cytoplasm, it was penetrated into a Calcein AM-stained HeLa cell, and fluorescence molecules of Calcein AM were successfully detected at the tip-end under an upright fluorescence microscope as shown in FIGS. 12A and 12B.

Figure 13:
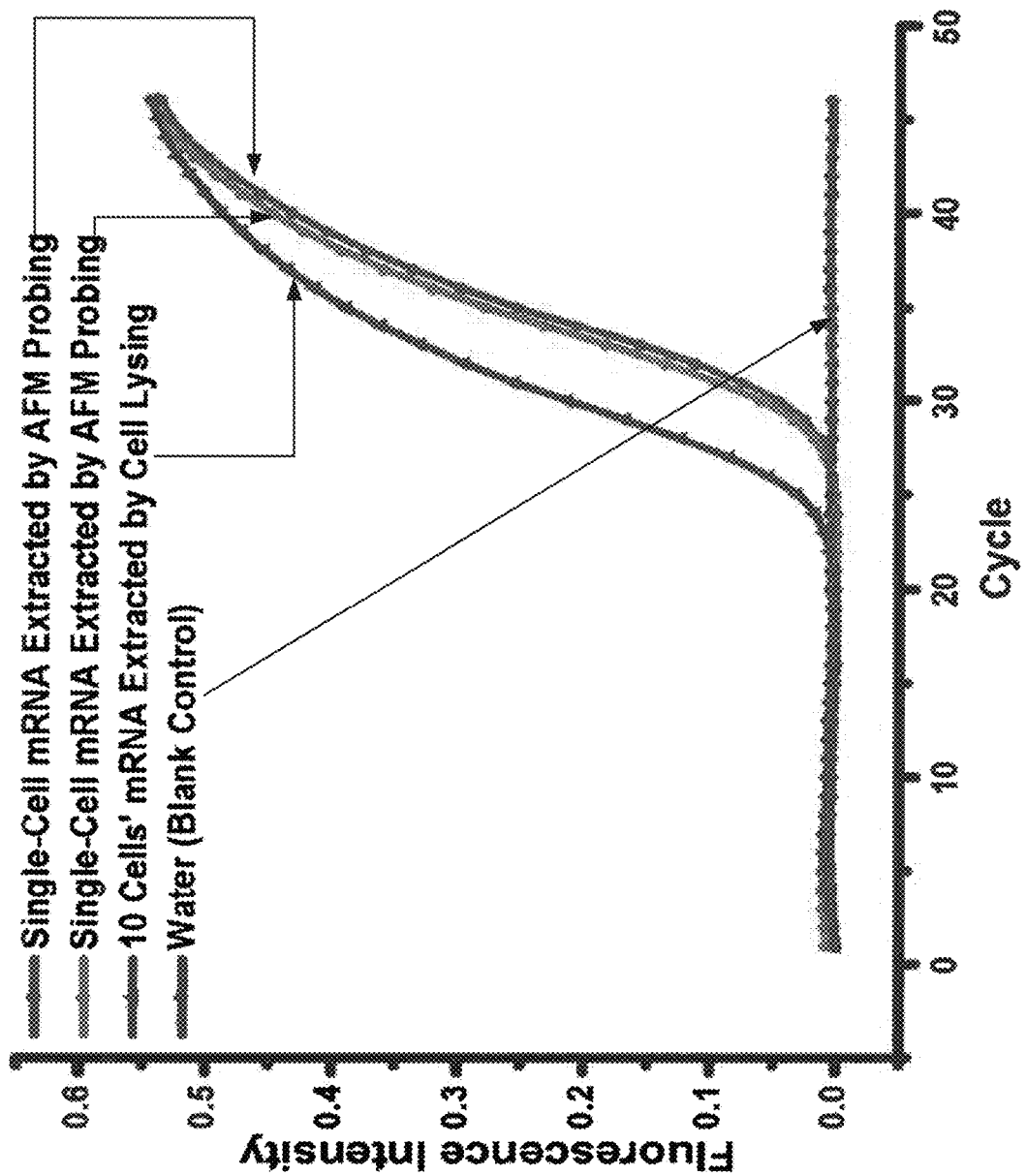
FIG. 13 illustrates RT-qPCR results of β-Actin mRNA extracted by selective AFM probing of single HeLa cells. Ct value of 10 cells' β-Actin mRNA molecules extracted by cell lysing kit is 23.50 (blue curve). Ct values of β-actin mRNA molecules extracted by AFM probing from two different HeLa cells were 27.48 (red curve) and 27.85 (green curve) respectively.

To demonstrate the feasibility of the assay, RT-qPCR results of β-actin mRNA probing from single HeLa cells are shown in FIG. 13. The quantity of β-actin mRNA molecules isolated from 10 HeLa cells by cell lysing mRNA extraction kit (blue line) was used as a reference, and had a Ct value (threshold cycle value—the PCR cycle at which a significant increase in PCR product is first detected) of 23.50. The Ct values of β-actin mRNA molecules from two different HeLa cells by the AFM-based extraction were 27.48 (red line) and 27.85 (green line) respectively. If assuming all the cell contents were accessed and qualified by cell lysing, based on the above results, mRNA extraction by the AFM probing from a single cell is estimated to have an efficiency of 56% of the cell lysing mRNA extraction kit.

Figure 14:
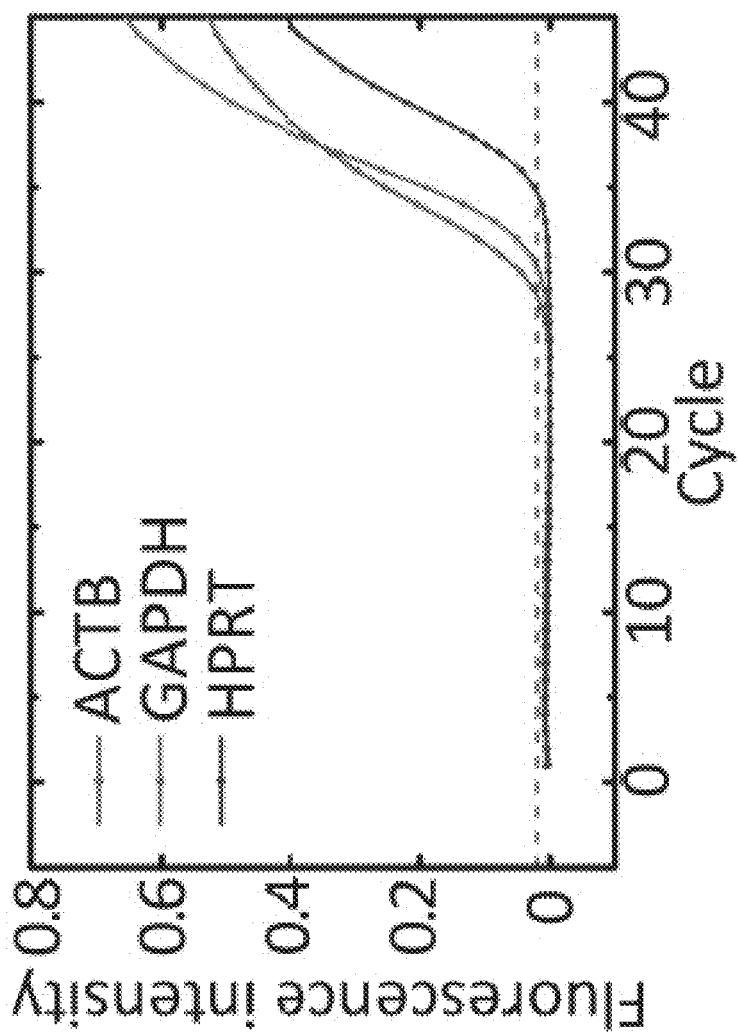
FIG. 14 illustrates RT-qPCR results of three housekeeping genes' mRNA molecules extracted from the target single HeLa cell at the applied AC field of 1.5 Vpp, 10 MHz. The threshold intensity was 0.02 indicated by the dashed line.

FIG. 14 shows the fingerprint of the expression levels of three housekeeping genes in a single HeLa cell under the applied AC field of 1.5 Vpp, 10 MHz: ACTB, a high-abundant gene; GAPDH, a medium-abundant gene; and HPRT, a low-expression gene (<102 copies per cell). For each target gene, 10% of the total cDNA product was transferred into the qPCR reaction volume, and SYBRGreen was used as the detection dye. With this current RT-qPCR setup, the expression levels of 10 different genes can be analyzed for each single cell.

However, more genes can be analyzed by increasing the efficiency of the qPCR assay, so that less amount of cDNA product is used for each gene. Also, sequence-specific fluorescent probes can replace SYBR-Green as the reporting dye, therefore different genes can be quantified at the same time.

As the applied voltage increased, the extracted number of mRNA molecules dramatically increased because of the stronger DEP force and higher mRNA molecule extraction efficiency associated with the increased voltage. Table I below illustrates a relative measurement of the amount of a target gene and the applied voltage.

TABLE I

|  | 1.1 V | 1.5 V | 1.9 V |
|---|---|---|---|
| ACTB | 31.4 ± 1.1 | 27.6 ± 0.5 | 26.5 ± 0.3 |
| GAPDH | 32.3 ± 0.7 | 29.4 ± 1.1 | 27.4 ± 0.5 |
| HPRT | NA | 33.8 ± 0.4 | 32.7 ± 0.9 |

Table I shows the cycle threshold (Ct) which presents a relative measurement of the amount of a target gene as the function of an applied voltage. The cycle threshold (Ct) can be found using qPCR. A lower Ct indicates a greater amount of the target gene. Under the AC field of 1.1 Vpp, 10 MHz, small numbers of ACTB (mean Ct=31.4, SD=1.1) and GAPDH (mean Ct=32.3, SD=0.7) mRNAs were successfully extracted without HPRT reading.

At the applied voltage of 1.5 and 1.9 Vpp, all three types of mRNAs were successfully extracted, but more ACTB and GAPDH were extracted than HPRT because of their intrinsic difference in expression levels. The control group, probing the empty trap inside the microfluidic channel, showed a negative reading with no amplification. The Ct value was higher compared to that of probing single cells in the media cultured in the petri dish where detached cells and debris from surrounding cells could stick on the tip when it dipped into the media.

As trapped cells were in close contact with the sealing film and were isolated by the physical traps, probing single cells in the microfluidic trapping array avoided the false-positive readings and cross contamination.

The absolute number of extracted mRNA molecules for different values of the applied voltage from 1.1 to 1.9 Vpp is shown in FIG. 15A. The number of extracted mRNA molecules was calculated based on the Ct values of the RT-qPCR experiment and the standard curves generated using synthetic oligomers of known concentrations and the mRNA capturing efficiency at different probing voltages was compared with the standard cell-lysing mRNA extraction method.

The average extracted copy number of ACTB from a single HeLa cell was 220±100 at 1.1 Vpp, 2580±690 at 1.5 Vpp, and 5440±940 at 1.9 Vpp, respectively. The average extracted copy number of GAPDH was 100±30 at 1.1 Vpp, 740±380 at 1.5 Vpp, and 2940±870 at 1.9 Vpp, respectively. As for the HPRT, although there was no reading at 1.1 Vpp, 40±10 molecules were captured at 1.5 Vpp, and 90±40 molecules were extracted out at 1.9 Vpp.

These results show that the presented approach has tunable target signal intensity according to the applied voltage. The ability to probe and detect the low-copy-number gene HPRT's mRNA molecules is critical as it benefits the analysis of target genes with low expression levels.

A cell viability assay was performed to see if the mRNA-extracted cell was still alive in the microfluidic channel. FIGS. 15B-1 to 15B-8 show the bright-field and fluorescence microscopic images of mRNA-extracted cells by DENT stained with Calcein AM. The mRNA-extracted cells were stained with Calcein AM after 12 h on-chip culture. Bright-field and fluorescence microscopic images of single cells show that live cells are distinguishable clearly by their intact morphology and bright green fluorescence.

The viability of mRNA-extracted cells probed under the application of lower voltages such as 1.1 and 1.5 Vpp was ~70%, which was similar to the viability of non-probed cells. However, the mRNA-extracted cells probed under the application of higher voltages like 1.9 Vpp had much weaker green fluorescence signal, which was because a large number of mRNA molecules were extracted by the AFM probe, affecting the cell metabolism.

No cell adherence or proliferation was observed during the culturing of mRNA-extracted cells, and most of the non-probed cells did not adhere to the microchannel bottom or proliferate, either. One possible reason for this can be attributed to the channel height which was approximately 18 µm, maybe too small to supply enough nutrition and space for growing cells.

In fact, most microfluidic devices which allow on-chip cell culture have a channel height over 100 µm. Although AFM probe caused a physical disturbance to the cell membrane, at the applied voltage of ~1.5 Vpp, cells maintained intact morphology and viability after mRNA extraction, while still providing substantial capturing efficiency achieved. Therefore, a field strength of approximately 1.5 Vpp was chosen for further marker-gene expression analysis.

On-chip Trapping of Carcinoma/Monocyte Mixtures and Cell Type Identification

Figure 16A:
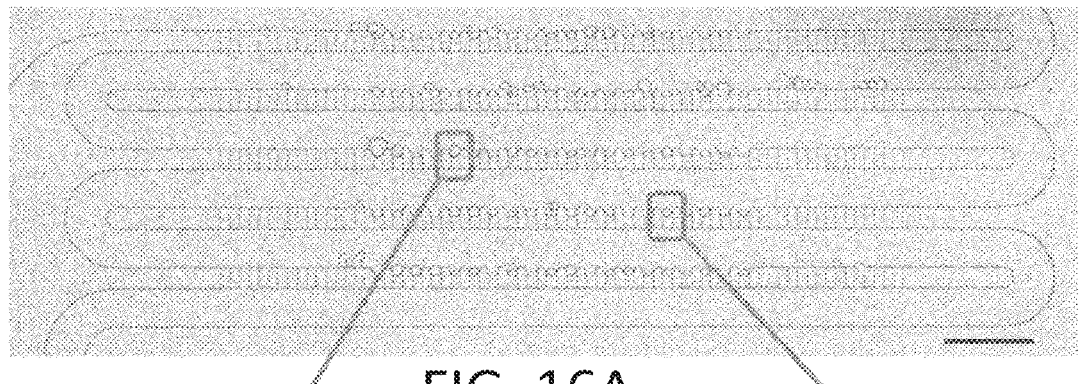
FIG. 16A is a bright-field image of trapping single cells of SK-BR-3 and U937 in the single-cell trapping array. The RT-qPCR fingerprints of the 4 target mRNAs (CD45, EpCAM, HER2 and ACTB) extracted by DENT from a trapped SK-BR-3 cell and a trapped U937 cell are shown in FIGS. 16B and 16C respectively.
Figure 16B:
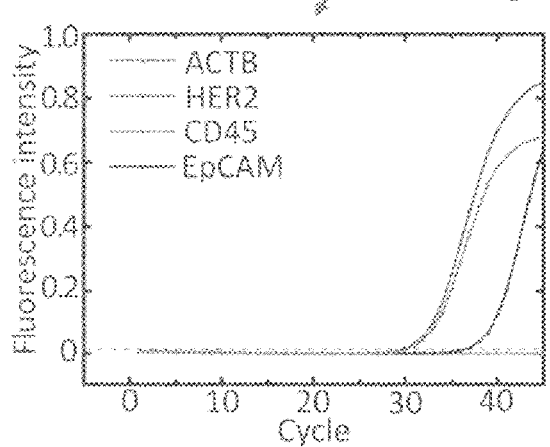
FIG. 16D is a gene-expression heatmap of trapped single SK-BR-3/U937 cells based on the RT-qPCR results of extracted mRNAs.
Figure 16C:
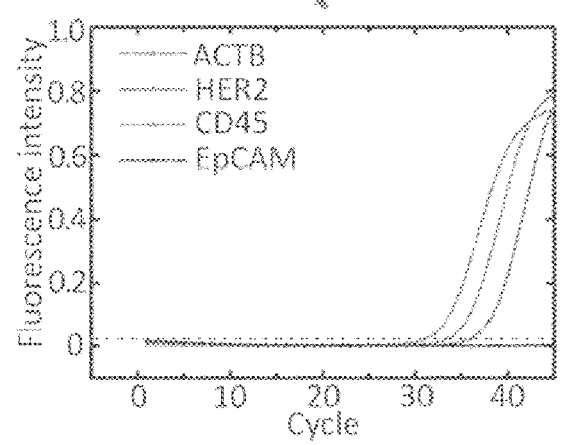

In order to develop a microfluidic cancer-cell-screening platform, the capability to identify single cancer cells individually among the normal blood cell populations is desirable. Therefore, the feasibility of selective mRNA extraction from cancer cells using the AFM probe was tested. A mixture of SK-BR-3 and U937 cells with a concentration of 1×10$^6$ cells per mL was introduced into an embodiment of a microfluidic device having a single-cell trapping array in accordance with the design principles discussed herein. Such an embodiment is shown in FIG. 16A. The sample mimics a blood sample that underwent primary CTC enrichment. SKBR-3 and U937 cells were trapped in the single-cell trapping array. In situ selective mRNA extraction from these two different types of single cells was performed. The RT-qPCR fingerprints of the four target mRNAs (CD45, EpCAM, HER2 and ACTB) extracted by the AFM probe from trapped SK-BR-3 cells are shown in FIG. 16B. The RT-qPCR fingerprints of the four target mRNAs (CD45, EpCAM, HER2 and ACTB) extracted by the AFM probe from trapped U937 cells are shown in FIG. 16C.

SK-BR-3, a human breast cancer cell line, expresses EpCAM (epithelial cellular adhesion molecule) as a CTC marker and over-expresses HER2 (human epidermal growth factor receptor 2) as a breast cancer cell marker. U937 is a human monocyte cell line, representing the dominant type of WBCs in human blood. It expresses CD45 as a leucocyte marker does not express EpCAM and should have a much lower HER2 expression level compared to breast cancer cells. The averaged single-cell mRNA probing results matched with the above marker-gene expression status reported in the literature.

With the applied AC field of 1.5 Vpp, 10 MHz, mRNAs of EpCAM (Ct=33.0, SD=1.5) and HER2 (Ct=27.1, SD=1.0) were successfully extracted from SK-BR-3 cells by the AFM probe tip without CD45 reading. Whereas for U937 cells, CD45 (Ct=32.6, SD=1.0) was extracted, but there was no EpCAM reading and a much lower HER2 reading (Ct=36.1, SD=1.3). ACTB from both of the two types of cells was quantified by RT-qPCR as the positive control. Based on the mRNA expression results plotted in FIGS. 16B and 16C, although the two types of cells were in a similar size range and could not be differentiated easily from the optical images, the RT-qPCR fingerprint of a specific single cell's mRNAs extracted by AFM probe tip revealed its specific gene expression levels and cell identity.

Figure 16D:
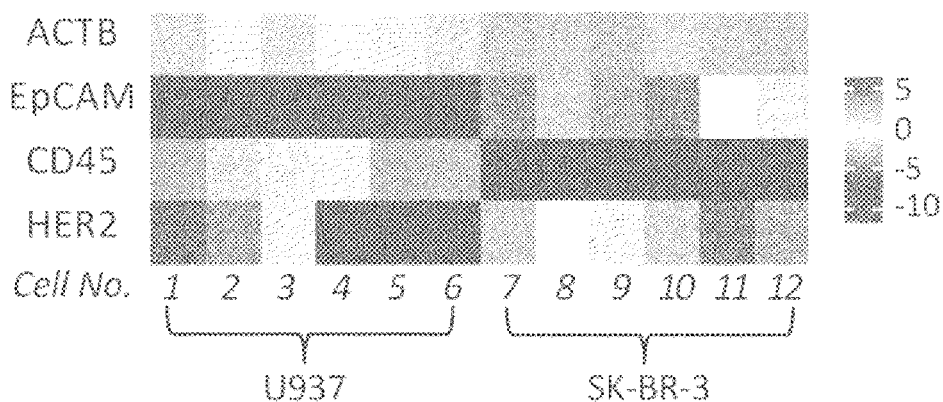

FIG. 16D shows the gene-expression heatmap representation of 12 single cells probed at the SK-BR-3/U937 cell mixture single-cell array. Some differences in gene expression exist between SK-BR-3 and U937 cells, and also cellular heterogeneity within the same population. With the ability to plot expression profiles of target cancer cells, it might be possible to identify the tissue origin of CTCs by the detection of organ-specific metastatic signatures from the cells, which is helpful to localize small, occult metastatic lesions and to guide further diagnostic and therapeutic strategies.

CONCLUSION

This application demonstrates the feasibility of a microfluidic device comprising a single-cell trapping array that can trap individual target cells in a biological sample and the use of a DENT (e.g., an AFM probe) to extract mRNA molecules. The extracted mRNA molecules were analyzed and various marker-genes' expressions of target single cells within the microfluidic trapping arrays were quantified. As the microfluidic device was sealed by a PDMS membrane having a thickness of less than or equal to about 1 microns, an external equipment such as an AFM nanoprobe, was able to penetrate into the microfluidic trapping array and be allowed to access a specific cell without cross-cell contamination and media evaporation.

This technique opens up new opportunities in the integration of microfluidic systems with various external elaborate instruments such as micro-pipettes and micro-injectors, so that more complicated manipulations and analyses of single cells could be performed inside a closed microfluidic environment. Samples can be processed—filtered, sorted, and enriched—before entering the "single-cell analysis" region on the chip. After analyzing, as the cells can retain viability, they can be released for further analysis and culturing, which opens up possibilities for moving beyond static snapshots of gene-expression profiles to understand how profiles change over time, e.g., real-time tracking of cell response to drug treatment.

Specifically, DEP-based mRNA extraction using DENT is a non-destructive method that does not require cell lysing or mRNA purification, and is sensitive enough to detect the expression level of low-copy-number genes (e.g. HPRT) within a single living cell among the cell population. In addition, as it works at the frequency specific for mRNAs and avoids the removal of cytosol, cells are protected from losing essential molecules.

In this work, we demonstrated single-cell trapping using only 100 cell traps. However, the number of single-cell entrapments can be easily scaled up by parallelization using multidevice processing and/or integrating a greater number of trapping arrays to process large sample volumes within a few minutes.

The scaled-up single-cell trapping array would be favored especially when applying the platform in CTC isolation and identification from whole blood, where CTCs and WBCs cannot be discriminated based on size and are trapped together. Benefiting from the multistep-integration feature of lab-on-a-chip systems, different sample-processing units can be integrated with this ultra-thin PDMS membrane-sealed single-cell array. For example, the presented microfluidic design can be easily combined with a variety of microfluidic modules for erythrocytes removal with high enrichment of CTCs, like blood filtration by inertial microfluidics, dielectrophoretic cell sorting, CTC capturing by antibody labeling, or immunomagnetic cell separators.

This capability is notably important when genetic profiling of the patient-derived CTCs from whole blood is required. Moreover, to achieve the collection and cultivation of post-probing cells for further studies such as monitoring gene expression at single-cell level according to the drug response, the mRNA extracted cells could be retrieved upon adapting various techniques, such as laser-induced bubble formation to displace a trapped cell localized negative dielectrophoretic force selective opening or closing of individual traps by microfluidic or logic gate.

In some embodiments, the trapping array can have a higher channel height to provide sufficient space and nutrition supply for long-term on-chip culturing of the probed cells. In some embodiments, a high-density array of DENTs could be fabricated by adapting the microneedle array fabrication techniques, e.g., DUV (deep ultraviolet) photolithography, DRIE (deep reactive ion etching) and crystalline wet etching. Therefore, hundreds of DENT probes can penetrate into hundreds of single cells each time with the combination of an automated micromanipulator, which allows for high-throughput single-cell transcriptomic analysis.

This application contemplates a method to extract mRNAs from single living cells in situ, which is a combination of the microfluidic single-cell trapping and the selective intracellular probing using DENT. An ultra-thin (~1 μm) PDMS membrane ensured a closed microfluidic environment, thus decreasing the chance that media were accidentally evaporated, and single mammalian cells were isolated individually. Approximately 100 single cells were successfully trapped in the size selective single-cell array within 20 s, with an average single-cell occupancy of 94±4%.

After the single-cell isolation within the trapping array, the DENT probe was accurately aligned with the target cell and penetrated through the ultra-thin PDMS membrane to extract mRNA molecules from cytoplasm with minimal damage by dielectrophoresis upon the application of AC field. The mRNA probing efficiency, which was related to the amplitude of the applied AC field, was analyzed based on the RT-qPCR results of three housekeeping genes, i.e., ACTB, GAPDH, and HPRT, after in situ mRNA extraction, with the post-probing cell viability examined by Calcein AM staining.

Also, fingerprinting of the cell-specific marker-genes (Ep-CAM, HER2 and CD45) and differentiation of two different cell lines (SK-BR-3 and U937) were successfully achieved using this approach. The integration of an external single-cell mRNA AFM DENT probe and the sealed microfluidic single-cell trapping array facilitates a powerful label-free and non-destructive single-cell probing platform with the capability of multi-step on-chip cell processing. The systems and methods described herein can be used in a variety of application areas such as stem cell biology, drug response monitoring, and cancer diagnostics.

The foregoing descriptions and following claims and related drawings and appendices A, B, and C of this provisional application shall be considered together as one disclosure of this application. Any and all descriptions set forth in the appendices A, B, and C included herewith shall be considered part of and are incorporated into the disclosure.

What is claimed is:

1. A lab-on-a-chip platform comprising:
   a microfluidic device comprising:
      an analysis region comprising a single cell trapping array; and
      a membrane sealing the analysis region from an ambient environment; and
      an external dielectric nanotweezer (DENT)
   wherein the membrane is configured to be punctured by the external DENT to form a hole therein to allow the external DENT to access the microfluidic sample.

2. The lab-on-a-chip platform of claim 1, wherein the external DENT comprises an atomic force microscope probe.

3. The lab-on-a-chip platform of claim 2, wherein the external DENT is configured to extract intracellular components from a trapped sample comprising an array of single cells in one or more microfluidic channels.

4. The lab-on-a-chip platform of claim 3, wherein the external DENT is configured to analyze mRNA expression levels of the extracted intracellular components.

5. The lab-on-a-chip platform of claim 1, wherein the external DENT comprises a micro-injector.

6. The lab-on-a-chip platform of claim 1, wherein the microfluidic device further comprises a microfluidic sample processing region upstream from the analysis region.

7. The lab-on-a-chip platform of claim 6, wherein the sample processing regions include sample sorting or sample separation region.

8. The lab-on-a-chip platform of claim 1, wherein the membrane is configured to be resealable such that after the hole is formed therein by the micro-manipulating instrument, the hole seals after removal of the micro-manipulating instrument.

9. The lab-on-a-chip platform of claim 1, wherein the membrane has a thickness of less than 5 μm.

10. The lab-on-a-chip platform of claim 1, wherein the membrane comprises an elastomer.

11. The lab-on-a-chip platform of claim 10, wherein the elastomer comprises PDMS.

12. A method of manufacturing a lab-on-a-chip platform according to claim 1, the method comprising:
   providing a microfluidic device comprising a microfluidic channel and a membrane configured to seal the microfluidic device from an ambient environment; and
   bonding the sealed microfluidic device on a substrate;
   wherein the membrane has a thickness less than 5 μm, and wherein the membrane encloses an analysis region of the microfluidic channel.

13. The method of claim 12, wherein the membrane comprises an elastomer.

14. The method of claim 13, wherein the elastomer comprises PDMS.

15. The method of claim 12, wherein at least one of an upstream sample flow region and a downstream sample flow region of the microfluidic channel is enclosed by the membrane.

16. The method of claim 12, wherein at least one of a sample processing region and a post-processing region of the microfluidic channel is enclosed by a structure that is thicker than the membrane.

17. A method of analyzing a sample, comprising:
   providing a lab-on-a-chip platform according to claim 1;
   disposing a sample containing cells on a portion of the analysis region for isolating the cells,
   disposing the microfluidic component on, under, beside or in an external DENT having a probe with a tip;

puncturing the membrane with the tip of the probe of the external micro-manipulating instrument; and manipulating an individual cell of the sample in the microfluidic channel using the tip of the probe.

18. The method of claim 17, wherein the membrane comprises an elastomer.

19. The method of claim 18, wherein the elastomer comprises PDMS.

20. The method of claim 17, wherein the external DENT comprises an atomic force microscope.

21. The method of claim 17, wherein the analysis region comprises a single cell trapping array for trapping a plurality of individual cells.

* * * * *